(12) United States Patent
Andersen et al.

(10) Patent No.: US 9,956,211 B2
(45) Date of Patent: May 1, 2018

(54) PHARMACEUTICAL COMPOSITIONS COMPRISING A LOCAL ANAESTHETIC SUCH AS BUPIVACAINE FOR LOCAL ADMINISTRATION TO THE MOUTH OR THROAT

(75) Inventors: Ove Andersen, Hellerup (DK); Stine Mogensen, Copenhagen SV (DK); Charlotte Treldal, Copenhagen O (DK); Torben Mogensen, Greve (DK); Sylvia Pulis, Copenhagen NV (DK)

(73) Assignee: MOBERG PHARMA AB, Bromma (SE)

( * ) Notice: Subject to any disclaimer, the term of this patent is extended or adjusted under 35 U.S.C. 154(b) by 403 days.

(21) Appl. No.: 14/114,669

(22) PCT Filed: Apr. 27, 2012

(86) PCT No.: PCT/EP2012/057864
§ 371 (c)(1),
(2), (4) Date: Jun. 12, 2014

(87) PCT Pub. No.: WO2012/146763
PCT Pub. Date: Nov. 1, 2012

(65) Prior Publication Data
US 2014/0296293 A1    Oct. 2, 2014

(30) Foreign Application Priority Data

Apr. 29, 2011 (DK) .................................. 2011 70213
May 6, 2011 (DK) .................................. 2011 70225

(51) Int. Cl.
| | | |
|---|---|---|
| A61K 31/445 | (2006.01) | |
| A61K 45/06 | (2006.01) | |
| A61K 9/00 | (2006.01) | |
| A61K 31/167 | (2006.01) | |

(52) U.S. Cl.
CPC .......... A61K 31/445 (2013.01); A61K 9/0056 (2013.01); A61K 31/167 (2013.01); A61K 45/06 (2013.01)

(58) Field of Classification Search
CPC ... A61K 9/0056; A61K 31/167; A61K 31/445
USPC .......................................... 514/330; 424/464
See application file for complete search history.

(56) References Cited

U.S. PATENT DOCUMENTS

| | | |
|---|---|---|
| 3,511,914 A | 5/1970 | Wolkoff et al. |
| 4,822,597 A | 4/1989 | Faust et al. |
| 4,853,212 A | 8/1989 | Faust et al. |
| 5,322,694 A | 6/1994 | Sixsmith |
| 5,332,576 A | 7/1994 | Mantelle |
| 5,399,354 A | 3/1995 | Ells et al. |
| 5,614,207 A | 3/1997 | Shah et al. |
| 5,912,007 A | 6/1999 | Pan et al. |
| 6,103,257 A | 8/2000 | Nisonoff |
| 6,183,775 B1 | 2/2001 | Ventouras |
| 6,194,003 B1 | 2/2001 | Day et al. |
| 6,264,981 B1 | 7/2001 | Zhang et al. |
| 6,488,963 B1 | 12/2002 | McGinity et al. |
| 6,699,908 B2 | 3/2004 | Sackler et al. |
| 6,790,855 B2 | 9/2004 | Pasternak et al. |
| 6,825,203 B2 | 11/2004 | Pasternak et al. |
| 6,921,541 B2 | 7/2005 | Chasin et al. |
| 7,163,705 B2 | 1/2007 | Johnson et al. |
| 7,452,523 B2 | 11/2008 | Hofmann et al. |
| 7,943,169 B2 * | 5/2011 | Domb ................... A61K 9/006 424/464 |
| 2001/0024658 A1 | 9/2001 | Chen et al. |
| 2002/0035096 A1 | 3/2002 | Lawter et al. |
| 2002/0052483 A1 | 5/2002 | Podolsky |
| 2002/0119104 A1 | 8/2002 | Rosenthal et al. |
| 2003/0049208 A1 | 3/2003 | Ream et al. |
| 2003/0087457 A1 | 5/2003 | Hughes |
| 2003/0114534 A1 | 6/2003 | Arsenault |

(Continued)

FOREIGN PATENT DOCUMENTS

| | | |
|---|---|---|
| DE | 20 2004 016 077 U1 | 11/2005 |
| DE | 20 2004 016 078 U1 | 11/2005 |

(Continued)

OTHER PUBLICATIONS

Jug et al. Preparation and solid-state characterization of bupivacaine hydrochloride cyclodextrin complexes aimed for buccal delivery. J. Pharm. Biomed. Anal. 52, pp. 9-18 (2010).*

(Continued)

*Primary Examiner* — Jeffrey S Lundgren
*Assistant Examiner* — Sara E Townsley
(74) *Attorney, Agent, or Firm* — LeClairRyan PLLC

(57) ABSTRACT

The present invention relates to compositions comprising a lipophilic local anaesthetic, preferably bupivacaine or a pharmaceutically active salt thereof, which are formulated for local administration to the mouth or throat of a subject. The compositions are useful in the treatment or alleviation of pain, burning or xerostomia of the oral cavity, pharynx, oral mucosa and pharyngeal mucosa or for use in providing local anesthesia of the oral cavity, pharynx, oral mucosa and pharyngeal mucosa. In particular in the treatment of pain, burning or xerostomia, which is caused by a disease such as oral mucositis, Burning Mouth Syndrome, Sjogren's syndrome, xerostomia, periodontitis, toothache, tonsillectomy, throat infection or mononucleosis, canker sores and aphthous stomatitis.

22 Claims, 3 Drawing Sheets

(56) References Cited

U.S. PATENT DOCUMENTS

| | | | |
|---|---|---|---|
| 2003/0175360 A1* | 9/2003 | Luzzatti | A61K 31/00 424/653 |
| 2003/0186884 A1 | 10/2003 | Markland, Jr. et al. | |
| 2003/0206866 A1 | 11/2003 | Wei | |
| 2004/0151771 A1 | 8/2004 | Gin et al. | |
| 2004/0167099 A1 | 8/2004 | Lawter | |
| 2004/0204366 A1 | 10/2004 | Pasternak et al. | |
| 2004/0220087 A1 | 11/2004 | Bar-Or | |
| 2004/0247669 A1* | 12/2004 | Gin | A23G 3/362 424/468 |
| 2004/0254128 A1 | 12/2004 | Kobayashi et al. | |
| 2005/0002993 A1 | 1/2005 | Goggin et al. | |
| 2005/0077497 A1 | 4/2005 | Anderson | |
| 2005/0152972 A1 | 7/2005 | Singh | |
| 2005/0271713 A1 | 12/2005 | Saito et al. | |
| 2006/0073189 A1 | 4/2006 | Pinney et al. | |
| 2006/0147498 A1 | 7/2006 | Jonsson et al. | |
| 2007/0031491 A1 | 2/2007 | Levine et al. | |
| 2007/0042027 A1 | 2/2007 | Haley | |
| 2007/0071806 A1 | 3/2007 | McCarty | |
| 2008/0085248 A1 | 4/2008 | Sela | |
| 2008/0269185 A1 | 10/2008 | Rothstein et al. | |
| 2008/0299050 A1 | 12/2008 | Bortz et al. | |
| 2009/0041676 A1 | 2/2009 | Hofmann et al. | |
| 2009/0081291 A1 | 3/2009 | Gin et al. | |
| 2009/0081294 A1 | 3/2009 | Gin et al. | |
| 2009/0149446 A1 | 6/2009 | Heldman | |
| 2010/0021683 A1 | 1/2010 | Junghans et al. | |
| 2010/0202981 A1 | 8/2010 | Pan | |
| 2010/0247453 A1 | 9/2010 | Jones | |
| 2010/0297265 A1 | 11/2010 | McKinney | |

FOREIGN PATENT DOCUMENTS

| | | |
|---|---|---|
| DE | 20 2009 000 862 U1 | 4/2009 |
| EP | 0 299 924 A2 | 1/1989 |
| EP | 0 778 768 B1 | 5/2004 |
| EP | 1 296 650 B1 | 3/2005 |
| EP | 1 559 418 A1 | 8/2005 |
| EP | 1 604 652 B1 | 1/2009 |
| EP | 1 917 982 B1 | 4/2010 |
| GB | 2 133 284 A | 7/1984 |
| WO | 89/10740 A1 | 11/1989 |
| WO | 94/08550 A1 | 4/1994 |
| WO | 96/40050 A1 | 12/1996 |
| WO | 97/42941 A2 | 11/1997 |
| WO | 00/35298 A1 | 6/2000 |
| WO | 01/82914 A2 | 11/2001 |
| WO | 01/89476 A1 | 11/2001 |
| WO | 02/00195 A2 | 1/2002 |
| WO | 02/087544 A1 | 11/2002 |
| WO | 03/082188 A2 | 10/2003 |
| WO | 2004/052336 A2 | 6/2004 |
| WO | 2004/070017 A2 | 8/2004 |
| WO | 2006/039961 A1 | 4/2006 |
| WO | 2006/075123 A1 | 7/2006 |
| WO | 2006/133412 A1 | 12/2006 |
| WO | 2007/025142 A2 | 3/2007 |
| WO | 2007/089652 A2 | 8/2007 |
| WO | 2007/110871 A2 | 10/2007 |
| WO | 2008/073324 A1 | 6/2008 |
| WO | 2009/042968 A1 | 4/2009 |
| WO | 2009/042969 A1 | 4/2009 |
| WO | 2009/043134 A1 | 4/2009 |
| WO | 2009/063223 A1 | 5/2009 |

OTHER PUBLICATIONS

B&B Compounding Pharmacy, "Pain Management Compounding," accessed from <http://www.bbpharmacy.com/paincompounding.html> on Apr. 12, 2013, 1 page.

Bernardo, M. V., et al., "Sustained Release of Bupivacaine from Devices Based on Chitosan," IL Farmaco, 2003, pp. 1187-1191, vol. 58.

Bhushan, N. V. V., et al., "A Comparison of the Efficacy of Topical Application of Lignocaine Hydrochloride 5% Gel and Bupivacaine Hydrochloride 5% Gel for Extraction of Teeth," Journal of Maxillofacial and Oral Surgery, Jun. 2010, pp. 119-126, vol. 9, No. 2.

Caphosol(R), "Caphosol Frequently Asked Questions," updated Oct. 31, 2011, accessed from <http://live.caphosol.com/en/PAT/caphosol-faq.aspx> on Mar. 12, 2013, 2 pages.

ClinicalTrials.gov, "Capsaicin Lozenges in Treating Patients with Mucositis Caused by Radiation Therapy," updated May 9, 2009, accessed from <http://clinicaltrials.gov/ct2/show/NCT00003610> on Apr. 12, 2013, 3 pages.

CollaRX(R), "Innocoll Files Investigational New Drug Application for its CollaRX(R) Bupivacaine Topical for the Treatment of Painful Chronic Skin Ulcers and Burns," News Archive Oct. 17, 2007, accessed from <http://innocollinc.com/news/47/232/Innocoll-Files-Investigational-New-Drug-Application> on Mar. 12, 2013, 2 pages.

Cousins, M. J., et al., "Table 3-1. Physicochemical Properties of Local Anesthetics," Neural Blockade in Clinical Anesthesia and Management of Pain, 3rd Edition, 1998, p. 56.

Hughes, L., et al., "A New Method of Characterizing the Buccal Dissolution of Drugs," Spring House: Rohm and Haas Research Laboratories, 2003, 4 pages.

Hung, T., et al., "Topical Bupivacaine in Paediatric Day-Case Tonsillectomy: A Prospective Randomized Controlled Trial," The Journal of Laryngology & Otology, Jan. 2002, pp. 33-36, vol. 116.

International Preliminary Report on Patentability issued for PCT/EP2012/057864, dated Oct. 29, 2013, 7 pages.

Kutscher, A. H., et al., "Long-Lasting Lozenges CU 701-1: Dissolution Duration Time at Home in Patients with Oral Mucosal Lesions," The Quarterly of the National Dental Association, Inc., Apr. 1969, pp. 76-77, vol. 27, No. 3.

McClenahan, W. U., et al., "Fatal Poisoning with Dibucaine Hydrochloride (Nuporal) Lozenges," Journal of the American Medical Association, Jun. 18, 1955, p. 565, vol. 158, No. 7.

Medical News Today, "New Treatment for Canker Sores," updated Mar. 27, 2007, accessed from <http://www.medicalnewstoday.com/releases/65931.php> on Apr. 12, 2013, 6 pages.

National Cancer Institute, "Supportive Care Statement for Health Professionals—Oral Complications of Chemotherapy and Head/Neck Radiation (PDQ(R))," accessed from <http://www.meb.uni-bonn.de/Cancernet/CDR0000062870.html> on Apr. 12, 2013, pp. 1-69.

Plewa, M. C., "Pediatric Aphthous Ulcers Treatment & Management," Medscape Reference, Drugs, Diseases & Procedures, 2013, pp. 1-7.

Pray, W. S., "Nonprescription Products," Nonprescription Product Therapeutics, 2005, p. 251.

Strichartz, G. R., et al., "Fundamental Properties of Local Anesthetics. II. Measured Octanol:Buffer Partition Coefficients and pKa Values of Clinically Used Drugs," Anesthesia & Analgesia, 1990, pp. 158-170, vol. 71.

Sveinsdottir, K., "Bupivacaine Lozenge Safety Study," Master's Thesis submitted Sep. 2013, 61 pages.

Seth, S. D., et al., Textbook of Pharmacology, 3rd Edition, 2009, Elsevier.

The United States Pharmacopeial Convention, "<711> Dissolution," Stage 6 Harmonization, Official Dec. 1, 2011, 8 pages.

Tomoda, K., et al., "Preparation and Properties of Carrageenan Microspheres Containing Allopurinol and Local Anesthetic Agents for the Treatment of Oral Mucositis," Colloids and Surfaces B: Biointerfaces, 2009, pp. 27-35, vol. 71, No. 1.

Wonnemann, M., et al., "Lidocaine 8 mg Sore Throat Lozenges in the Treatment of Acute Pharyngitis. A New Therapeutic Option Investigated in Comparison to Placebo Treatement," Arzneimittel-Forschung (Drug Research), 2007, pp. 689-697, vol. 57, No. 11.

De Neve et al., "Aspiration Pneumonia: An Underestimated Cause of Severe Respiratory Failure in Patients with Haematological Malignancies and Severe Oral Mucositis?," Acta Clinica Belgica 65-6:416-419 (2010).

(56) References Cited

OTHER PUBLICATIONS

Shaoul et al., "Evaluation of Topical Pharyngeal Anaesthesia by Benzocaine Lozenge for Upper Endoscopy," Alimentary Pharmacology & Therapeutics 24:687-694 (2006).
Xylocaine (Lidocaine) Drug Information: Warnings and Precautions—Rx List Entry (www.rxlist.com/xylocaine-drug/warnings-precautions.html) (Oct. 13, 2014—last reviewed on Rx List Jan. 10, 2011).
Lalla et al., "Management of Oral Mucositis in Patients with Cancer," Dent. Clin. North Am. 52(1):61-77 (2008).
Gad, S.C., "Pharmaceutical Manufacturing Handbook: Production and Process," vol. 10, pp. 252-253 (2008).
Chan et al., "Flavored Anesthetic Lozenge Versus Xylocaine Spray Used as Topical Pharyngeal Anesthesia for Unsedated Esophagogastroduodenoscopy: A Randomized Placebo-Controlled Trial", Surg Endosc, 24:897-901, (2010).
Ayoub et al., "Lidocaine Lollipop as Single-Agent Anesthesia in Upper GI Endoscopy", Gastrointestinal Endoscopy, 66(4):786-793.
Sudhakar et al., "Buccal Bioadhesive Drug Delivery—A Promising Option for Orally Less Efficient Drugs," Journal of Controlled Release 114:15-40 (2006).
Dinakar et al., Chapter 47: Clinical Applications of Local Anesthetics, In: Essential Clinical Anesthesia, Cambridge University Press (2011), at p. 288.

* cited by examiner

PHARMACEUTICAL COMPOSITIONS COMPRISING A LOCAL ANAESTHETIC SUCH AS BUPIVACAINE FOR LOCAL ADMINISTRATION TO THE MOUTH OR THROAT

REFERENCE TO RELATED APPLICATIONS

This application is a U.S. national stage application of International Patent Application No. PCT/EP2012/057864, filed Apr. 27, 2012, and claims the benefit of priority of Danish Application No. PA201170225 filed May 6, 2011, and Danish Application No. PA201170213 filed Apr. 29, 2011. The entire contents of the above applications are hereby incorporated by reference.

FIELD OF INVENTION

The present invention relates to compositions suitable for the treatment or alleviation of pain, burning or xerostomia particularly of the oral cavity. Pain, burning or xerostomia of the oral cavity may be caused by many different factors and/or conditions. Such conditions include oral mucositis, Burning Mouth Syndrome, Sjögren's syndrome, xerostomia, periodontitis, toothache, tonsillectomy, throat infection or mononucleosis, canker sores and aphthous stomatitis. Oral mucositis may for example be due to a subject undergoing treatment for cancer.

The compositions of the present invention comprises an effective amount of a local anaesthetic, which is preferably bupivacaine or a pharmaceutically active salt thereof, and are formulated for local administration to the mouth or throat of a subject.

The present invention also relates to compositions being used for providing local anesthesia of the oral cavity, pharynx, oral mucosa and pharyngeal mucosa.

BACKGROUND OF INVENTION

Pain control is of prime importance to anyone treating many different diseases and medical conditions. Proper pain relief imparts significant physiological and psychological benefits to the patient. Not only does effective pain relief mean a smoother, more pleasant recovery (e.g., mood, sleep, quality of life, etc.) with earlier discharge from medical/surgical/outpatient facilities, but it may also reduce the probability of the acute pain state progressing to a chronic pain syndrome.

Mucositis is the painful inflammation and ulceration of the mucous membranes lining the digestive tract, usually as an adverse effect of chemotherapy and radiotherapy treatment for cancer. Mucositis can occur anywhere along the gastrointestinal (GI) tract, but oral mucositis refers to the particular inflammation and ulceration that occurs in the mouth. Oral mucositis is a common and often debilitating complication of cancer treatment.

Pain associated with oral mucositis can be extremely debilitating and can lead to poor oral food intake. In extreme cases, patients may require feeding tubes if the ulceration continues to advance.

Local anesthetics are agents that prevent transmission of nerve impulses without causing unconsciousness. They act by binding to fast sodium channels from within (in an open state). Local anesthetics can be either ester or amide based.

Bupivacaine hydrochloride is an amide-based local anesthetic and is a well established active ingredient. Bupivacaine has been used for more than 20 years in daily clinical practice as a local anesthetic, for both surgery and postoperative pain treatment. Bupivacaine is also referred to as 1-butyl-N-(2,6-dimethylphenyl)piperidine-2-carboxamide ($C_{18}H_{28}N_2O$).

Currently, there is no efficient treatment to offer patients suffering from pain associated with oral mucositis and other similar conditions. There is thus a great need for effective remedies which may help these patients by increasing their food intake and increase their oral hygiene.

Surprisingly the inventors have found that compositions comprising bupivacaine, or other lipophilic local anaesthetics, or a pharmaceutically active salt thereof are very useful in the treatment or alleviation of pain, burning or xerostomia of the oral cavity, pharynx, oral mucosa and pharyngeal mucosa. The compositions are very useful especially for patients suffering from oral mucositis, and may increase food intake and increase oral hygiene.

SUMMARY OF INVENTION

According to one aspect, the invention provides a sustained-release composition comprising a local anaesthetic amide compound having an octanol/water partition coefficient of at least 100, more preferably at least 300, or a salt thereof, formulated for local administration to the mouth or throat of a subject for use in the treatment or alleviation of pain, burning or xerostomia of the oral cavity, pharynx, oral mucosa and pharyngeal mucosa or for use in providing local anesthesia of the oral cavity, pharynx, oral mucosa or pharyngeal mucosa.

The partition coefficient is measured as in Strichartz et al (1990) *Anesth. Analg.* 71, 158-170, using the "standard aqueous medium" disclosed therein (150 mM NaCl, 5 mM 2-(N-morpholino)ethanesulphonic acid, 5 mM morpholinopropane sulphonic acid and 5 mM (3-cyclohexylamino)-propane sulphonic acid in water), adjusted to pH7.4, at 25° C.

The compound is preferably bupivacaine, ropivacaine, etidocaine or levobupivacaine or a pharmaceutically active salt of any of those compounds, such as the hydrochloride.

These compounds have the following partition coefficients: bupivacaine and levobupivacaine 346; ropivacaine 115; etidocaine 800. In comparison, benzocaine has a partition coefficient of only 81, and lidocaine only 2.4. (All these data are taken from "Neural Blockade in Clinical Anesthesia and Management of Pain", Eds. Cousins M J and Bridenbaugh P O, $3^{rd}$ Edition, Lippincott-Raven, Philadelphia, 1998, Table 3-1.)

Local anaesthetics having a partition coefficient of over 300 are preferred, and bupivacaine (optionally as the hydrochloride) is especially preferred. All disclosures herein of aspects of the invention, including formulations, processes and uses, apply specifically to bupivacaine (optionally as the HCl salt) as well as to the other named local anaesthetics and their salts.

It might have been expected that such lipophilic compounds would be absorbed very quickly. However, we have found that the compounds are absorbed over a surprisingly long time and therefore provide a prolonged period of efficacy.

The pain, burning or xerostomia can, for example, be caused by a disease selected from the group consisting of oral mucositis, Burning Mouth Syndrome, Sjögren's syndrome, xerostomia, periodontitis, toothache, tonsillectomy, throat infection or mononucleosis, canker sores and aphthous stomatitis.

The anesthesia can, if desired, be provided before diagnostic upper gastrointestinal endoscopy, intubation or dental procedures.

The local anaesthetic or a pharmaceutically active salt thereof is preferably present in an amount of 0.1 to 75 mg (preferably 0.1 to 50 mg), for example 5 mg, 10 mg, 25 mg or 50 mg, per oral dosage form.

The concentration of the local anaesthetic or salt thereof in the composition may, for example, be 0.1% to 5% (w/w).

The sustained-release composition is preferably formulated to provide sustained release of the local anaesthetic or pharmaceutically active salt thereof over time period of at least 1, 2, 5, 10, 15, 20, 25, 30, 35, 40, 45, 50 or 55 minutes, more preferably at least 60 minutes, for example from about 70 minutes, such as up to about 80 minutes, for example up to about 90 minutes, such as up to about 100 minutes, for example up to about 2 hours, such as up to about 3 hours, for example up to about 4 hours, such as up to about 5 hours, for example up to about 6 hours. All of these values can be permutated to represent upper and lower limits of ranges of release time, for example the range can be 20-40 or 20-60 minutes.

All references herein to release times refer to the composition being tested in "Apparatus 1", as described in the US Pharmacopeial Convention s.771 (Dissolution) (Official Date 1 Dec. 2011), with a nominal one liter capacity, using a fitted cover, and operated at 37° C. with a rotation speed of 50 rpm according to Method A for Extended Release Dosage Forms, except that a simulated saliva medium is used, consisting of 12 mM $KH_2PO_4$, 40 Mm NaCl and 1.5 mM $CaCl_2$ adjusted to pH 6.2 with NaOH. Six apparently identical dosage forms are tested at the same time and complete dissolution (i.e. the end of the period of release) is deemed to have occurred when at least four dosage forms have completely dissolved.

The composition is solid and can, for example, be in a form selected from the group consisting of microspheres (when formed into tablets), chewable tablets, chewing gum, patches, tablets, cachets, lozenges, pastilles and dispersible granules (when formed into tablets). The sustained-release composition is preferably in a form selected from the group consisting of lozenges, including but not limited to powder-based lozenges, syrup-based lozenges, granulated lozenges and lozenges with an applicator (i.e. a lollipop), buccal tablets and chewing gums.

A compressed granular product containing 5 to 25 mg of bupivacaine is a preferred embodiment of the invention and is suitable for the treatment of acute conditions, such as oral mucositis, over a relatively short period, for example 1, 2, 3 or 4 weeks, with administration 3, 4 or 5 times a day.

A syrup-based cast lozenge containing 2 to 5 mg bupivacaine is also a preferred embodiment of the invention and is suitable for use over extended periods, for example several years, being administered ad lib, but typically again 3, 4 or 5 times a day.

The latter embodiment has several advantages: 1) it is much easier to mask the inherent taste of the bupivacaine or other local anaesthetic and to produce the lozenge with a variety of tastes; 2) lozenges produced in that way can last even longer in the mouth; and 3) syrup-based lozenges seem not so dry for the patient when they suck them. Thus this product fits the needs of the chronic pain indications, using lower amounts of local anaesthetic, but on a regular basis. Moreover, this product also helps to alleviate the "dry mouth" sensation the patients are suffering from. It thus combines pain relief with saliva production through sucking on the lozenge, which is a novel effect.

It is furthermore surprising that the bupivacaine retains full activity despite being heated at up to 180° C. during the casting process.

The local anaesthetic or a pharmaceutically active salt thereof may be the only active ingredient, or there may also be a second active ingredient, for example selected from the group consisting of antimicrobial agents such as antiviral agents, antimycotic agents and antibiotics; anti-inflammatory agents, biologics, chemotherapy/anticancer agents, cough and cold preparations including but not limited to antitussives, expectorants, decongestants, fluoride-releasing compounds and other dental hygiene products, saliva stimulating agents, other anaesthetic agents and anti-emetics. Lidocaine and benzocaine are preferably not present.

A further aspect of the invention provides these compositions for use for the treatment or alleviation of pain, burning or xerostomia of the oral cavity, pharynx, oral mucosa and pharyngeal mucosa and/or for the increased stimulation of saliva and/or for the reduction of inflammation in the oral cavity, pharynx, oral mucosa and pharyngeal mucosa.

A still further aspect of the invention provides a method for the treatment or alleviation of pain, burning or xerostomia of the oral cavity, pharynx, oral mucosa and pharyngeal mucosa comprising locally administering any of the defined pharmaceutical compositions to the mouth or throat of a subject.

Drug delivery to the mouth and pharynx is non-invasive and well tolerated. Furthermore, drugs administered by the mouth require neither technical equipment (e.g. infusion pumps), nor extensive expertise or training.

Saliva secretion facilitates the dissolution of drugs administrated to the mouth and pharynx. When anesthetizing the pharynx, the swallowing of the saliva is utilized as the drug passes the pharynx and thereby induces the requested effect. The present invention provides a continuous release from a slow drug release delivery system such as a lozenge, in addition to swallowing of the saliva, allows a homogeneous and slow spread of the drug to the mucosa of the oropharynx and the posterior third of the tongue.

Yet a further aspect of the invention relates to a method for producing a compressed lozenge comprising the steps of:
(a) passing the defined local anaesthetic, filler or binder, sweetening agent and aroma through a sieve,
(b) mixing the ingredients,
(c) adding glidant or lubricant and gently mixing with the other excipients,
(d) compressing the lozenge.
(e) thereby producing a compressed lozenge.

Typical sieve mesh sizes (i.e. the pore sizes) range from 75 μm to 1400 μm, with 100-150 μm, such as about 75 μm, being preferred. In step (c), the glidant or lubricant should be mixed gently with the other ingredients for a suitable period so that it does not stick to the particles of the other ingredients, making them unable to stick to each other, otherwise it would not be possible to make compressed lozenges. This process is well within the normal skills of a formulator of lozenges. In step (d), pressures of 50-200 Newtons are typically used, preferably 120-130 Newtons. Again, selecting a suitable pressure is well within the normal skills of a formulator of lozenges.

The invention further relates to methods of producing lozenges wherein one step comprises a granulation step. Granulation may be performed by wet granulation and/or dry granulation.

Another aspect of the invention relates to a method for producing a syrup-based lozenge comprising the steps of:

parboiling sweet soluble dietary fibre containing short chain fructo-oligosaccharides to a temperature of 140-160° C. to liquidise the fibre, pouring out liquidized fibre, adding aroma powder and kneading it into the fibre mass until dissolved, adding the local anaesthetic, preferably bupivacaine or a pharmaceutically active salt thereof, and kneading it into the fibre mass until dissolved, adding the mass to a cylinder, thereby casting syrup-based lozenges, each containing a therapeutically effective amount of the local anaesthetic.

A further, and most preferred, method comprises:

granulating a mixture of a local anaesthetic, preferably bupivacaine or a pharmaceutically active salt thereof, with binder or filler, sweetening agent and aroma to form granules;

mixing the granulates with glidant; and compressing the lozenge.

Another aspect of the invention relates to such a composition which is packaged in a manner that promotes shelf-life and maximizes stability of the excipients.

DETAILED DESCRIPTION OF THE INVENTION

Figure 1:
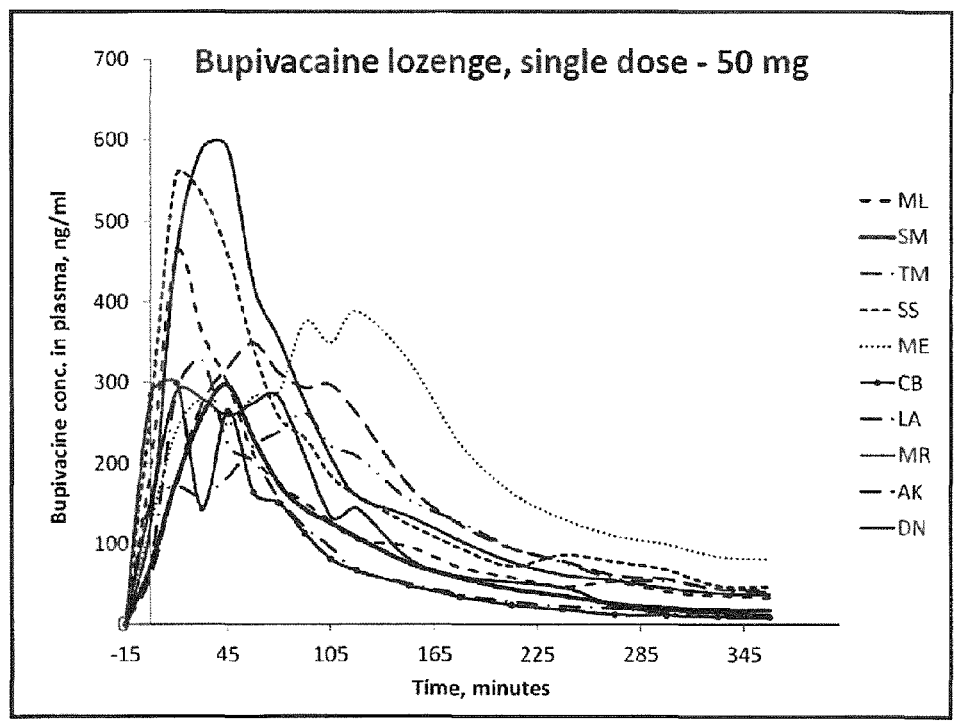
FIG. 1 shows the bupivacaine serum concentrations after administration of bupivacaine lozenges with a total dose of 50 mg bupivacaine (Example 2, Study I).

A "dosage form" is intended to mean a single unit comprising a particular dose of the local anaesthetic, such as for example one lozenge.

"Optional" or "optionally present", as in an "optional additive" or an "optionally present additive", means that the subsequently described component (e.g., additive) may or may not be present, so that the description includes instances where the component is present and instances where it is not.

By "pharmaceutically acceptable" is meant a material that is not biologically or otherwise undesirable, e.g., the material may be incorporated into a dosage form of the invention without interacting in a deleterious manner with any of the other components of the dosage form formulation. The term "biocompatible" is used interchangeably with the term "pharmaceutically acceptable." When the term "pharmaceutically acceptable" is used to refer to a pharmaceutical excipient, it is implied that the excipient has met the required standards of toxicological and manufacturing testing and/or that it is included on the Inactive Ingredient Guide prepared by the U.S. Food and Drug Administration.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of an undesirable condition. Thus, for example, "treating" a patient involves prevention of an adverse condition in a susceptible individual as well as treatment of a clinically symptomatic individual by inhibiting or causing regression of the condition.

By an "effective" amount of the local anaesthetic is meant a nontoxic but sufficient amount of the agent to provide the desired effect. The amount of beneficial agent that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation.

The terms fillers, binders or binding agents are used interchangeably and are intended herein to mean a material used to bind other materials together. A filler may be used to increase the mass or volume of a pharmaceutical formulation and may for example be used in formulation with small amounts of active ingredients and/or to reduce variation in mass of the formulations and/or to enhance handling of the formulation during production. Even with larger amounts of active ingredients a filler may be added to enhance compression properties. Binders or binding agents may be used to enhance the technical properties of the formulation and/or to influence the release of the active ingredient from the administered dose. Said technical properties may for example be the mechanical resistance of the formulation, e.g. a higher mechanical strength and/or lower friability during the manipulations the formulation undergoes during for example preparation and transport etc. The terms "glidants" or "lubricants" or "antisticking agents" are used interchangeably and are intended herein to mean a substance that is added to a powder to improve its flowability.

Glidants enhance flow, lubricants reduce friction and antisticking agents prevent adhesion. All may be used to improve the ability to dose the formulation and/or the distribution of pressure during compression and/or reduce the mutual friction between particles and/or granulates as well as friction to stamps during and after compression.

An applicator is a tool or a device for applying a substance such as a drug formulation, for example a lollipop.

A "cast lozenge" is intended to mean a "syrup-based", "high-boiled" or "hard candy" type of lozenge. A "base" means the base of a cast lozenge, comprising for example candy base or sweet dietary fibre.

An "adhesion modifier" means a compound that modifies the adhesion of a composition and is most often used in mucoadhesive formulations. The adhesion modifier may be an adhesion-increasing agent or an adhesion-reducing agent, and may be a mucoadhesive agent, an ingestible solvent such as ethyl acetate, a mineral oil or a vegetable oil, for example. The mucoadhesive effect may be obtained by hydrophilic polymers that swell or stick with water and make hydrogen bonds with the viscous mucous protein mucin which is found on epithelial cells. Mucoadhesive formulations are thus kept in direct contact with mucous membrane over a longer period of time, which will enhance the fraction of absorbed active agent and present loss of active agent with saliva to the gut. A "flavor stabilizer" is a compound that stabilizes the flavour of a composition. A "pH-adjusting agent" is a compound that adjusts the pH of a composition.

A "preservative" is a naturally occurring or synthetic substance that is added to products such as foods, pharmaceuticals, paints, biological samples, wood, etc. to prevent decomposition by microbial growth or by undesirable chemical changes. A "colorant" is a compound which when added to something else causes a change in colour. Colorants are often used for example to enhance the appearance of a non-colored formulation.

An "absorption enhancer" is a compound that enhances the absorption of a compound, for example in the oral cavity and/or enhances bioavailability of poorly absorbed drugs.

A "taste masking agent" is an agent that may be used to mask an unpleasant taste of for example a pharmaceutical composition. Various methods are available to mask undesirable taste of the drug, e.g. coating of drug particles with inert agents or by formation of molecular complexes that lowers drug solubility and thereby decreases the intensity of the undesirable taste.

A "surfactant" or "wetting agent" is a compound that lowers the surface tension of a liquid, the interfacial tension between two liquids, or the interfacial tension between a liquid and a solid, and may be used to ensure a faster wetting of the compressed lozenge and thus faster disintegration and release.

Antimicrobial agents include antibiotics, anti-fungal agents and anti-viral agents. The terms "antimycotic" and "anti-fungal" agents are used interchangeably and are intended herein to mean any agent that destroys, inhibits or prevents the growth of fungi. An "anti-viral agent" as used herein is intended to mean any agent that is useful for treating viral infections. An "anti-inflammatory agent" is an agent that reduces inflammation.

The terms "mucolytic agent" and "expectorant" are used interchangeably and mean any agent which dissolves thick mucus and is usually used to help relieve respiratory difficulties. An "antiemetic" is a drug that is effective against vomiting and nausea.

Xerostomia is the medical term for the subjective complaint of dry mouth due to a lack of saliva. In a particular embodiment of the invention, the pain, burning or is caused by toothache also known as odontalgia or, less frequently, as odontalgy. Toothache is an aching pain in or around a tooth. In most cases toothaches are caused by problems in the tooth or jaw, such as cavities, gum disease, the emergence of wisdom teeth, a marginally cracked tooth, infected dental pulp (necessitating root canal treatment or extraction of the tooth), jaw disease, or exposed tooth root.

Tonsillectomy is a surgical procedure in which the tonsils are removed from either side of the throat. Throat infection or pharyngitis is an infection of the throat or pharynx. In most cases it is painful. It is the most common cause of a sore throat.

Local Anesthetics

Local anesthetics are agents that prevent transmission of nerve impulses without causing unconsciousness. They act by binding to fast sodium channels from within (in an open state). Local anesthetics can be either ester- or amide-based, although only amides are used in the present invention as the primary anaesthetic. The local anesthetic to be used with the present invention may, for example, be selected from the group of compounds identified in Table 1.

TABLE 1

Amide local anesthetics

| Name | Formula | Structure |
| --- | --- | --- |
| Bupivacaine hydrochloride: | $C_{18}H_{28}N_2O$ $C_{18}H_{29}ClN_2O$ | 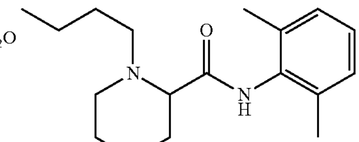 |
| Levobupivacaine (Chirocaine) hydrochloride: | $C_{18}H_{28}N_2O$ $C_{18}H_{29}ClN_2O$ | 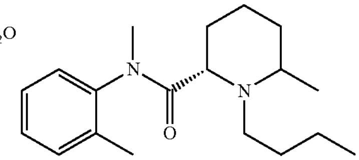 |
| Ropivacaine hydrochloride: | $C_{17}H_{26}N_2O$ $C_{17}H_{27}ClN_2O$ | 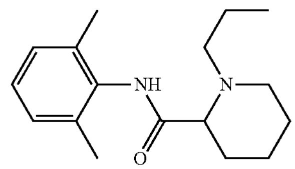 [SMILES: CCCN1CCCCC1C(=O)Nc1c(C)cccc1C] |

In some embodiments the compositions of the invention comprise only one local anaesthetic but in other embodiments the compositions of the invention may comprise one or more, such as two or more, three or more, or four or more local anaesthetics. The number of local anaesthetics generally does not exceed six, five or four. The compositions may comprise one or more, two or more, three or more or four or more local anaesthetics as the only active ingredient(s), but in some embodiments other active ingredients may also be present (described in detail herein below).

In a particularly preferred embodiment the local anesthetic is bupivacaine or derivatives and/or pharmaceutically active salts hereof.

Bupivacaine binds to the intracellular portion of sodium channels and blocks sodium influx into nerve cells, which prevents depolarization. Since pain transmitting nerve fibres tend to be thinner and either unmyelinated or lightly myelinated, the agent can diffuse more readily into them than into thicker and more heavily myelinated nerve fibres like touch, proprioception, etc.

Preclinical safety data showed no special risks for humans, evaluated from conventional investigations of safety pharmacology, toxicity after single as well as repeated dosage, reproduction toxicity, mutagenic potential and local toxicity, besides those that can be expected on the basis of the pharmacodynamic effect of high bupivacaine doses (e.g. effect on CNS and cardio toxicity).

Topical bupivacaine is used in tonsillectomy for both children and adults. In a study (Hung et al., 2002), bupivacaine-soaked swabs (approx. 50-75 mg bupivacaine) were tightly packed into the tonsillar fossae after the removal of tonsils, without any signs of toxic symptoms.

Bupivacaine is marketed under the trade names Marcain, Marcaine, Sensorcaine and Vivacaine.

Levobupivacaine is the (S)-(−)-enantiomer of bupivacaine, with a longer duration of action and producing less vasodilation. A biodegradable controlled-release drug delivery system for post surgery is also in development. Levobupivacaine and any pharmaceutically active salts hereof, such as the hydrochloride salt, are included within the scope of the present invention.

Ropivacaine is a bupivacaine derivative having an n-propyl group in place of the n-butyl group. The term 'ropivacaine' includes both the racemate and the marketed S-enantiomer. Both ropivacaine and the salt ropivacaine hydrochloride are encompassed within the scope of the present invention.

Derivatives of Local Anaesthetics

Bupivacaine or any of the other local anaesthetics described herein may be in the form of a salt, ester, amide, prodrug, active metabolite, isomer, analog, or the like, provided that the salt, ester, amide, prodrug, active metabolite, isomer, or analog is pharmaceutically acceptable and retains at least some degree of the desired activity. Salts, esters, amides, prodrugs, metabolites, analogs, and other derivatives of bupivacaine may be prepared using standard procedures known to those skilled in the art of synthetic organic chemistry and described, for example, by J. March, Advanced Organic Chemistry: Reactions, Mechanisms and Structure, 4th Edition (New York: Wiley-Interscience, 1992). In all cases, the compound should have an octanol/water partition coefficient of at least 100.

For example, acid addition salts are prepared from bupivacaine or any of the other local anaesthetics described herein in the form of a free base using conventional methodology involving reaction of the free base with an acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base.

Conversely, preparation of basic salts of acid moieties that may be present on an active agent may be carried out in a similar manner using a pharmaceutically acceptable base such as sodium hydroxide, potassium hydroxide, ammonium hydroxide, calcium hydroxide, trimethylamine, or the like. Preparation of esters involves transformation of a carboxylic acid group via a conventional esterification reaction involving nucleophilic attack of an RO" moiety at the carbonyl carbon. Esters can be reconverted to the free acids, if desired, by using conventional hydrogenolysis or hydrolysis procedures. Amides may be prepared from esters, using suitable amine reactants, or they may be prepared from an anhydride or an acid chloride by reaction with ammonia or a lower alkyl amine.

Other derivatives and analogs of bupivacaine or any of the other local anaesthetics described herein may be prepared using standard techniques known to those skilled in the art of synthetic organic chemistry, or may be deduced by reference to the pertinent literature. In addition, chiral active agents may be in isomerically pure form, or they may be administered as a racemic mixture of isomers.

Formulations

Sustained-Release Compositions

The sustained release dosage form is formulated in a manner sufficient to form a composition that includes the various components of a sustained release dosage form, such that when positioned in an oral cavity the composition slowly dissolves or degrades or erodes and thereby lubricates the oral cavity and delivers the local anaesthetic over a prolonged period of time, for instance up to about 15 minutes, up to about 30 minutes, up to about an hour, up to about 2 hours, up to about 3, hours, up to about 4 hours, up to about 5 or 6 hours or more.

The composition of the invention may be completely dissolved after being in the mouth for a period of 30 seconds, for example about 1 minute, such as about 2 minutes, for example about 3 minutes, such as about 4 minutes, for example about 5 minutes, such as about 10 minutes, for example about 15 minutes, such as about 20 minutes, for example about 25 minutes, such as about 30 minutes, for example about 35 minutes, such as about 40 minutes, for example about 45 minutes. In a preferred embodiment the composition of the invention is completely dissolved after about 20 minutes.

In some embodiments the sustained-release composition is formulated to provide sustained release of the local anaesthetic over a time period of about from 1 minute, such as from about 2 minutes, for example from about 5 minutes, such as from about 10 minutes, for example from about 15 minutes, such as from about 20 minutes, for example from about 25 minutes, such as from about 30 minutes, for example from about 35 minutes, such as up to about 40 minutes, for example from up to 45 minutes, such as up to about 50 minutes, for example up to about 55 minutes, such as from about 60 minutes, for example from about 70 minutes, such as up to about 80 minutes, for example up to about 90 minutes, such as up to about 100 minutes, for example up to about 2 hours, such as up to about 3 hours, for example up to about 4 hours, such as up to about 5 hours, for example up to about 6 hours.

In specific embodiments the sustained-release composition is formulated to provide sustained release of the local anaesthetic over a time period of about from 1 minute to about 30 minutes, such as from about 2 minutes, for example from about 5 minutes, such as from about 10 minutes, for example from about 15 minutes, such as from about 20 minutes, to about 60, 45 or 30 minutes in each case.

In a preferred embodiment the sustained-release composition according to the present invention is formulated to provide a local anesthetic effect for approximately 45-60 minutes.

The composition of the invention may thus be completely dissolved after being in the mouth for a period of 30 seconds, for example about 1 minute, such as about 2 minutes, for example about 3 minutes, such as about 4 minutes, for example about 5 minutes, such as about 10 minutes, for example about 15 minutes, such as about 20 minutes, for example about 25 minutes and may thus provide relief from pain, burning or xerostomia in a period of about from 1 minute, such as from about 2 minutes, for example from about 5 minutes, such as from about 10 minutes, for example from about 15 minutes, such as from about 20 minutes, for example from about 25 minutes, such as from about 30 minutes, for example from about 35 minutes, such as up to about 40 minutes, for example from up to 45 minutes, such as up to about 50 minutes, for example up to about 55 minutes, such as from about 60 minutes, for example from about 70 minutes, such as up to about 80 minutes, for example up to about 90 minutes, such as up to about 100 minutes, for example up to about 2 hours, such as up to about 3 hours, for example up to about 4 hours, such as up to about 5 hours, for example up to about 6 hours.

When the compositions of the present invention are formulated as a sustained-release composition such compositions may comprise one or more release rate modifiers selected from the group consisting of water-soluble polymers such as sodium carboxymethylcellulose, water-insoluble polymers such as ethylcellulose and ingestible solvents including but not limited to ethyl acetate, ethanol, glycerol, glycerol esters. However, it is preferred for the compositions not to comprise ethylcellulose.

Further useful rate modifiers may be selected from sugars such as saccharine or sorbitol, naturally occurring compounds such as acacia gum; sodium alginate; gelatin; starches such as potato, wheat or corn starch; pre-gelatinized starch; microcrystalline cellulose; or synthetic or semi-synthetic compounds such as sodium carboxymethylcellulose, methylcellulose, hydroxypropylmethylcellulose, polyvidone or polyethyleneglycol.

Hydrophilic/hydrophobic excipients, compression pressure and the surface area of the composition, preferably a lozenge, affect the rate of release of the local anaesthetic and are thus selected to best achieve the types of sustained release of the local anaesthetic set out above.

Compressed Powder Lozenge

A compressed powder lozenge may for example comprise one or more excipients such as diluents including fillers or binders selected from the group consisting of mannitol, celluloses, lactose, starches, calcium salts, polyvinylpyrrolidine, gelatine, sugars and sugar alcohols. In certain embodiments, the particle size and/or average particle diameter of the binder may be varied so as to control the dissolution, degradation or erosion characteristics of the overall dosage form. Specifically, in certain embodiments, such as where a more cohesive matrix is desired, the binder for use in conjunction with the subject invention may be a composition having a substantially uniform particle diameter. In certain embodiments, such as where a less cohesive matrix is desired, the film forming binder may be a more coarse composition having an average diameter particle size with a desired degree of non-uniformity. In this manner, by varying the average diameter particle size of the binder composition to be formulated into the matrix, a final dosage form with a desired dissolution/degradation/erosion pattern may be formulated.

A compressed powder lozenge may for example comprise one or more glidants or lubricants selected from the group consisting of talc, magnesium stearate, polyethyleneglycol (macrogol), and silicon dioxide.

One or more artificial or natural sweeteners may be incorporated into the formulation so as to enhance the taste of the composition. Any sweetener well known in the art may be used. A compressed/powder lozenge may for example comprise one or more non-sugar sweetening agents selected from the group consisting of aspartame, sorbitol, xylitol, isomalt, saccharin, sodium saccharin, calcium saccharin, sucralose, acesulfame-K, steviol and its glycosides such as stevioside (steviosin), mannitol, erythritol, lactitol, ammonium glycyrrhizin, glycerol and mixtures thereof. A compressed powder lozenge may for example comprise one or more sugar sweetening agents selected from the group consisting sucrose, fructose, or dextrose.

One or more aroma compounds, also known as odorant, fragrance or flavour, may be incorporated into the formulation so as to enhance the taste of the composition. A compressed powder lozenge may for example comprise one or more aromas selected from the group consisting of natural or synthetic aromatic compounds including but not limited to fruit aromas, powders including but not limited to liquorice powder, vanillin and menthol, pharmaceutical acceptable essential oils and chemical constituents of essential oils.

Compressed Granulated Lozenge

In other particular embodiments of the invention the compositions of the present invention are formulated as compressed granulated lozenges. A granulated lozenge is intended to mean a lozenge wherein the local anaesthetic is granulated prior to compression. Such a process may be useful to formulate a lozenge with a longer release time or to use other form of taste-masking as those described for the other types of lozenges. These compositions are comprised within the definition of a sustained-release composition.

A compressed granulated lozenge may for example comprise one or more diluents including fillers or binders. The binder may be polyvinylpyrrolidine and the polar solvent may be an alcoholic solvent such as industrial methylated spirit (IMS) or isopropanol (IPA). The amount of binding agent should be sufficient to ensure that the granule is robust enough not to be damaged during storage and transportation of the granule.

The granule may be dried prior to blending with the molten lozenge-forming composition to remove the polar solvent. The lozenge-forming composition may be a sugar-based or sugar alcohol-based composition. If the lozenge-forming composition is sugar-based, it may comprise a single sugar (e.g. sucrose) or a mixture of sugars (e.g. a mixture of sucrose and glucose). If the lozenge-forming composition is sugar-alcohol based it may comprise sorbitol, xylitol, maltitol, maltitol syrup, lactitol, mannitol or mixtures thereof which may be in the form of the free sugar alcohols, derivatives thereof or mixtures thereof.

Cast Lozenge

In other particular embodiments the compositions of the present invention are formulated as cast lozenges. A cast lozenge is intended to mean "syrup based", "high-boiled" or "hard candy" types of lozenge. These compositions are comprised within the definition of a sustained-release composition.

A cast or syrup-based lozenge comprises a base selected from the group consisting of one or more sweet soluble dietary fibre containing short chain fructo-oligosaccharides, other soluble dietary fibre, crystalline sugar, candy base, isomalt or stevia. In a preferred embodiment the base comprises sweet soluble dietary fibre containing short chain fructo-oligosaccharides, particularly Actilight®.

A cast or syrup-based, or compressed, lozenge may for example comprise one or more aromas selected from the group consisting of natural aroma, essential oils including but not limited to citrus and mint oils, chemical constituents of essential oils including but not limited to hydrocarbons, particularly terpenes and sesquiterpenes, organic acids, alcohols, aldehydes, ketones, esters, phenol ethers, ammonium chloride, liquorice powder, menthol, peppermint oil or any fruit flavours or aromas.

One or more taste or taste enhancing ingredients may also be added to the cast or syrup-based lozenge or a compressed lozenge. These are designed to enhance the existing flavours of products without adding any new tastes or flavours of their own. These include but are not limited to saccharose, glutamic acid (an amino acid) and its salts (E620 glutamic acid, E621 monosodium glutamate, MSG, E622 monopotassium glutamate, E623 calcium diglutamate, E624 monoammonium glutamate, E625 Magnesium diglutamate); guanylic acid (a ribonucleotide) and its salts (E626 guanylic acid, E627 disodium guanylate, sodium guanylate, E628 dipotassium guanylate, E629 calcium guanylate); inosinic acid (a ribonucleotide) and its salts (E630 inosinic acid, E631 disodium inosinate, E632 dipotassium inosinate, E633 calcium inosinate); mixtures of guanylate and inosinate (E634 calcium 5'-ribonucleotides, E635 disodium 5'-ribonucleotides); maltol and ethyl maltol (E636 maltol; E637 ethyl maltol); amino acids and their salts (E640 glycine and its sodium salt, E641 L-leucine).

The compositions of any type may for example comprise 0.01-10% (w/w) or 0.1-5% (w/w), such as 0.05% (w/w), 0.8% (w/w), 1.0% (w/w), 0.6 to 1%, for example 0.7 to 0.9%, preferably 0.8% (w/w), 1.5 to 2% (w/w) (e.g. 1.6%), 1.4 to 1.8, for example 1.5 to 1.7%, preferably 1.6% (w/w), 2 to 4% (w/w), 3.8 to 4.2%, for example 3.9 to 4.1%, preferably 4% (w/w), 4 to 6% (w/w), 6 to 8% (w/w), or 8 to 10% (w/w) of the local anaesthetic, the remainder being one or more excipients.

In certain embodiments the composition according to the present invention comprises:
- 0.01-10% (w/w) a local anaesthetic, preferably bupivacaine or a pharmaceutically active salt hereof,
- 60-85% (w/w) filler or binder,
- 0-10% (w/w) glidant or lubricant,
- 0-10% (w/w) non-sugar sweetening agent and
- 0-20% (w/w) aroma.

In a particular specific embodiment the composition according to the present invention comprises:
- 0.1-5% (w/w) a local anaesthetic, preferably bupivacaine or a pharmaceutically active salt hereof,
- 70-85% (w/w) filler or binder,
- 0-10% (or 1-10%) (w/w) glidant or lubricant,
- 0.5-5% (w/w) non-sugar sweetening agent and
- 5-20% (w/w) aroma.

In an even more specific embodiment said composition is a sustained release composition which comprises:
- 0.1-5% (w/w) of the local anaesthetic,
- 70-85% (w/w) filler or binder,
- 0-10% (w/w) glidant or lubricant,
- 0.5-5% (w/w) non-sugar sweetening agent and
- 5-20% (w/w) aroma.

In a very specific embodiment, particularly (but not exclusively) wherein said composition is in the form of a cast lozenge the composition comprises:
- 0.01-5% (w/w) of the local anaesthetic,
- 70-95% (w/w) base,
- 3-20% (w/w) aroma.

Further Excipients

The compositions of the present invention, of whichever type (compressed, cast etc), may comprise additional excipients to those already described herein above. If additional excipients are included, then the percentages of the ingredients given above refer to the composition of those ingredients and do not include the additional excipients.

A composition of the present invention may for example comprise: one or more flavor stabilizers such as starch; one or more pH-adjusting agents including but not limited to acids, bases and buffer systems; one or more preservatives including but not limited to antioxidants and antimicrobial agents; and/or one or more disintegrants including but not limited to glycerol, sugars and other polyols.

One or more colorants may be added if a colored dosage form is desired, particularly in the case of the cast lozenges. The colorant(s) may be natural colorants, such as pigments and dyes obtained from mineral, plant, and animal sources, such as riboflavin and betanin. Examples of natural colorants include red ferric oxide, yellow ferric oxide, annattenes, alizarin, indigo, rutin, and quercetin. Synthetic colorants may be used and may include an FD&C or D&C dye, e.g., an approved dye selected from the so-called "coal-tar" dyes, such as a nitroso dye, a nitro dye, an azo dye, an oxazine, a thiazine, a pyrazolone, a xanthene, an indigoid, an anthraquinone, an acridine, a rosaniline, a phthalein, a quinoline, or a "lake" thereof, i.e., an aluminum or calcium salt thereof. Useful colorants may be food colorants in the "GRAS" (Generally Regarded As Safe) category.

A composition of the present invention may for example comprise one or more vaso-constrictors such as caffeine. The reduced blood flow prevents the local anesthetic being removed too quickly, and so deepens and prolongs the anesthesia. Furthermore the reduced blood flow delays diffusion of the anesthetic agent to the rest of the body, which reduces the risk of toxic reactions.

A composition of the present invention may for example comprise one or more absorption enhancers; one or more taste masking agents; one or more surfactants or wetting agents; one or more swelling agents; one or more applicators or binders such as starch sodium octenyl succinate.

Further Active Ingredient

In a preferred embodiment of the invention the pharmaceutical compositions of the invention contains the local anaesthetic as the only active ingredient. However, in certain embodiments the composition may also comprise a further active ingredient. In one preferred embodiment the bupivacaine or a pharmaceutically active salt hereof are comprised in a composition or a kit of parts that further comprises a therapeutic effective amount of a further active ingredient.

The further active ingredient may be selected from the group consisting of antimicrobial agents such as antiviral agents, anti-fungal agents and antibiotics; anti-inflammatory agents, biologics, chemotherapy/anticancer agents, cough and cold preparations including but not limited to antitussives, expectorants, decongestants, fluoride-releasing compounds and other dental hygiene products, saliva stimulating agents, other anesthetic agents and antiemetics.

Antimicrobial agents include antibiotics, anti-fungal agents and anti-viral agents.

In patients being treated with chemotherapy and radiation, steps may be taken to prevent bacterial infection within the oral cavity. For this reason, in an optional embodiment, the compositions of the invention may comprise an antibiotic component.

Such antibiotic components may be of the macrolide type and may be selected from the group consisting of erythromycin, azithromycin, clarithromycin, dirithromycin, roxithromycin carbomycin A, josamycin, kitasamycin, oleandomycin, spiramycin, troleandomycin, tylosin, cethromycin, ansamycin and telithromycin. In one aspect the antibiotic is erythromycin.

Once ulcerations develop inside the mouth, local oral bacteria colonize the wound and release cell wall products into the mucosa, resulting in an amplification of a tissue destructive cycle. The antibiotic component such as erythromycin, limits such bacterial colonization.

Alternatively, the antibiotic may be any of the following, alone or in combination: an aminoglycoside, for example amikacin, gentamicin, kanamycin, neomycin, netilmicin, streptomycin or tobramycin; a carbacephem, for example loracarbef; a carbapenem, for example ertapenem, imipenem/cilastatin or meropenem; a cephalosporin (first generation), for example cefadroxil, cefazohn or cephalexin; a cephalosporin (second generation), for example cefaclor, cefamandole, cefoxitin, cefprozil or cefuroxime; a cephalosporin (third generation), for example cefixime, cefdinir, cefditoren, cefoperazone, cefotaxime, cefpodoxime, ceftazidime, ceftibuten, ceftizoxime or ceftriaxone; a cephalosporin (fourth generation), for example cefepime; a glycopeptide, for example teicoplanin or vancomycin; a penicillin, for example amoxicillin, ampicillin, azlocillin, carbenicillin, cloxacillin, dicloxacillin, flucloxacillin, mezlocillin, nafcillin, penicillin, piperacillin or ticarcillin; a (poly)peptide, for example bacitracin, colistin or polymyxin B; a quinolone, for example ciprofloxacin, enoxacin, gatifloxacin, levofloxacin, lomefloxacin, moxifloxacin, norfloxacin, ofloxacin or trovafloxacin; a sulfonamide, for example mafenide, prontosil, sulfacetamide, sulfamethizole, sulfanamide, sulfasalazine, sulfisoxazole, trimethoprim or trimethoprim-sulfamethoxazole; a tetracycline, for example demeclocycline, doxycycline, minocycline, oxytetracycline or tetracycline;—any nother antibiotic, for example chloramphenicol, clindamycin, ethambutol, fosfomycin, furazolidone, isoniazid, linezohd, metronidazole, nitrofurantoin, pyrazinamide, quinupristin/dalfopristin, rifampin or spectinomycin.

Patients being treated with chemotherapy and radiation are immuno-compromised, which leads to not only increased risk of viral and bacterial infection but also to an increased risk of fungal infection, thus advancing the risk and degree of oral mucositis, nystatin and amphotericin B act to prevent and limit the degree of fungal infection The antimycotic or anti-fungal agent may be selected from nystatin, amphotericin B or an imidazole, for example miconazole, ketoconazole, clotrimazole, econazole, mebendazole, bifonazole, butoconazole, fenticonazole, isoconazole, oxiconazole, sertaconazole, sulconazole, thiabendazole or tiaconazole; a triazole, for example fluconazole, itraconazole, ravuconazole, posaconazole or voriconazole; an allylamine, for example terbenafine, amorolfine, naftifine or butenafine; or an echinocandin, such as caspofungin or micafungin; or any combinations thereof.

The anti-viral and antibacterial agent may be selected from aciclovir, amoxycillin, antituberculosis medicines, atomoxetine, azathioprine, brivudine, famciclovir, ganciclovir, soniazid (INH), rifampicin, pyrazinamide, valaciclovir, valganciclovir, zidovudine (or other antiretrovirals e.g., against HIV), and the like.

Anti-inflammatory agents that may be included as a further active ingredient in a composition of the present invention include by way of example: NSAIDS (nonsteroidal anti-inflammatory agents), such as ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, fenbufen and tiaprofenic acid; acetylsalicylic acid, apazone, diclofenac, difenpiramide, diflunisal, etodolac, flufenamic acid, indomethacin, ketorolac, meclofenamate, mefenamic acid, nabumetone, phenylbutazone, piroxicam, sulindac, and tolmetin; and corticosteroids such as hydrocortisone, hydrocortisone-21-monoesters (e.g. hydrocortisone-21-acetate, hydrocortisone-21-butyrate, hydrocortisone-21-propionate, hydrocortisone-21-valerate, etc.), hydrocortisone-17,21-diesters (e.g. hydrocortisone-17,21-diacetate, hydrocortisone-17-acetate-21-butyrate, hydrocortisone-17,21-dibutyrate, etc.), alclometasone, dexamethasone, flumethasone, prednisolone, methylprednisolone, clobetasol, betamethasone fluocinonide, mometasone, triamcinolone acetonide, and the like.

Additionally, the further active ingredient may be a fluoride-releasing compound or other dental hygiene product that promotes healthy teeth and gums, or that exhibits other utility in the "dental" context. For instance, a fluoride-releasing dosage form may be prepared by incorporating a source of fluoride ion as a further active ingredient. Fluoride-releasing agents are well known and include sodium monofluorophosphate, sodium fluoride, and stannous fluoride. Fluoride-containing dosage forms may contain xylitol as a sweetener, as xylitol may potentiate the action of the fluoride.

The compositions of the present invention may also comprise any chemotherapy/anticancer agent, such as doxycycline gel, chlorhexidine chip and minocycline microspheres.

The compositions of the present invention may also comprise cough and cold preparations, including but not limited to antitussives, expectorants and decongestants. Antitussives may be selected from dextromethorphan (DXM), codeine, antihistamines, antihistamine-decongestant combinations, benzonatate and guaifenesin. A mucolytic agent or expectorant is any agent which dissolves thick mucus and is usually used to help relieve respiratory difficulties. An expectorant or mucolytic agent according to the present invention may include but is not limited to guaifenesin, Althea root, antimony pentasulfide, creosote, guaiacolsulfonate, ipecacuanha (syrup of ipecac), levoverbenone, potassium iodide, senega, tyloxapol, acetylcysteine, ambroxol, bromhexine, carbocisteine, domiodol, dornase alfa, eprazinone, erdosteine, letosteine, mesna, neltenexine, sobrerol, stepronin and tiopronin. A decongestant according to the present invention may include but is not limited to ephedrine, Levo-methamphetamine, naphazoline, oxymetazoline, phenylephrine, phenylpropanolamine, propylhexedrine, pseudoephedrine, synephrine and tetrahydrozoline.

The compositions of the present invention may also comprise saliva stimulating agents including but not limited to pilocarpine, cevimeline, anethole trithione, carboxymethyl hydroxyethylcellulose solutions, yohimbine, human interferon alfa (IFN-α) substitutes based on linseed polysaccharide (Salinum®), xanthan gum polysaccharide (Xialine®), antimicrobial peptides, Entertainer's Secret®, Glandosane®, Moi-Stir®, Optimoist®, Saliva Substitute®, Salivart®, Salix®, V. A. Oralube®, Xero-Lube® artificial saliva, mucopoly-saccharide solutions, MouthKote®, Biotene® products and Oralbalance®.

The compositions of the present invention may comprise an antiemetic, which is a drug that is effective against vomiting and nausea. Antiemetics in the present context are typically used to treat the side effects of anaesthetics, and chemotherapy directed against cancer. Antiemetics include 5-$HT_3$ receptor antagonists such as dolasetron (Anzemet), granisetron (Kytril, Sancuso), ondansetron (Zofran), tropisetron (Navoban), palonosetron (Aloxi), mirtazapine (Remeron), an antidepressant that also has antiemetic effects; dopamine antagonists such as domperidone, droperidol, haloperidol, chlorpromazine, promethazine, prochlorperazine, metoclopramide (Reglan), alizapride, prochlorperazine (Compazine, Stemzine, Buccastem, Stemetil, Phenotil); neurokinin 1 (NK1) receptor antagonists such as aprepitant (Emend), casopitant; antihistamines ($H_1$ histamine receptor antagonists) such as cyclizine, diphenhydramine (Benadryl), dimenhydrinate (Gravol, Dramamine), meclozine (Bonine, Antivert), promethazine (Pentazine, Phenergan, Promacot), hydroxyzine; cannabinoids such as cannabis, dronabinol (Marinol), synthetic cannabinoids such as nabilone (Cesamet) or the JWH series, Sativex; benzodiazepines such as midazolam, lorazepam; anticholinergics such as hyoscine (also known as scopolamine); steroids such as dexamethasone and other antiemetics including but not limited to trimethobenzamide, ginger, emetrol, propofol, peppermint, muscimol.

The compositions of the present invention may comprise additional anesthetic agents. The additional anesthetic agent may be selected, for example, from menthol, benzocaine, butambenpicrate, chlorprocaine, cocaine, dibucaine, dimethisoquin, dyclonine, etidocaine, hexylcaine, hexylresorcinol, ketarine, lidocaine, mepivacaine, phenol, phenolate, pramoxine, procaine, tetracaine, tripelennamine, xylocalne, and pharmaceutically acceptable salts thereof (e.g., dimethisoquin hydrochloride, pramoxine hydrochloride). However, it is preferably not benzocaine or lidocaine.

Dose

The effective dosage of the local anaesthetic is intended to mean a dose that provides relief from pain, burning or xerostomia of the oral cavity, pharynx, oral mucosa and pharyngeal mucosa or to provide localized anesthesia of the oral cavity, pharynx, oral mucosa and pharyngeal mucosa.

The administration of one dosage of the local anaesthetic is intended to provide relief from pain, burning or xerostomia of the oral cavity, pharynx, oral mucosa and pharyngeal mucosa in a patient in need thereof for a suitable amount of time according to the nature of pain, burning or xerostomia.

The administration of the local anaesthetic according to the present invention is preferably a frequent administration during the day. Accordingly, the daily dosage may be administered in divided dosages of 1 to 10 individual dosages daily, preferably 2 to 5 times daily, for example around 3 times daily. The specific number of daily applications may be correlated to the individual way of administration and the severity of the symptom in question. The preferred treatment is a treatment where the medicament is present in the mucosal membrane as constant as possible due to the theory that the individual factors involved in the maintenance of the symptoms are constantly produced in the affected mucosal membrane during the illness.

As stated herein above, the compositions of the invention may be completely dissolved after being in the mouth for a period of 30 seconds, for example about 1 minute, such as about 2 minutes, for example about 3 minutes, such as about 4 minutes, for example about 5 minutes, such as about 10 minutes, for example about 15 minutes, such as about 20 minutes, for example about 25 minutes and may thus provide relief from pain, burning or xerostomia in a period of about from 1 minute, such as from about 2 minutes, for example from about 5 minutes, such as from about 10 minutes, for example from about 15 minutes, such as from about 20 minutes, for example from about 25 minutes, such as from about 30 minutes, for example from about 35 minutes, such as up to about 40 minutes, for example from up to 45 minutes, such as up to about 50 minutes, for example up to about 55 minutes, such as from about 60 minutes, for example from about 70 minutes, such as up to about 80 minutes, for example up to about 90 minutes, such as up to about 100 minutes, for example up to about 2 hours, such as up to about 3 hours, for example up to about 4 hours, such as up to about 5 hours, for example up to about 6 hours.

The dose of the local anaesthetic is in the range of from 0.01 to 75 mg per dosage form, preferably 0.01 to 50 mg, for example 0.05 mg, 0.1 mg, 0.5 mg, 1.0 mg, 2 mg, 3 to 5 mg, 3 to 7 mg, 4 to 6 mg, 5 mg, 5 to 7 mg, 7 to 9 mg, 8 to 12 mg, 9 to 11 mg, 10 mg, 10 to 12 mg, 12 to 15 mg, 15 to 20 mg, 20 to 25 mg, 23 to 27 mg, 24 to 26 mg, 25 mg, 25 to 30 mg, 30 to 35 mg, 35 to 40 mg, 40 to 45 mg, 45 to 50 mg, 50 to 55 mg, 55 to 60 mg, 60 to 65 mg, 65 to 70 mg, or 75 mg per dosage form.

In specific preferred embodiments of the present invention the local anaesthetic is present in the composition in an amount of 5 mg, 10 mg or 25 mg.

A composition comprising a dose of the local anaesthetic of 25 mg may be dissolved completely after about 4 minutes, for about 5 minutes, such as about 10 minutes, for example about 15 minutes, and provide relief from pain, burning or xerostomia in a period from about 25 minutes, such as from about 30 minutes, for example from about 35 minutes, such as up to about 40 minutes, for example from up to 45 minutes, such as up to about 50 minutes, for example up to about 55 minutes, such as from about 60 minutes, for example from about 70 minutes, such as up to about 80 minutes, for example up to about 90 minutes, such as up to about 100 minutes, for example up to about 2 hours, such as up to about 3 hours, for example up to about 4 hours, such as up to about 5 hours, for example up to about 6 hours.

A composition comprising a dose of the local anaesthetic of 5 mg may be dissolved completely after about the same periods as for the 25 mg dose but will probably dissolve completely in no more than 4 hours (instead of potentially 5 or 6 hours), and a composition comprising a dose of the local anaesthetic of 50 mg may similarly be dissolved completely after any of the same periods as for the 25 mg dose but might last for up to 7 or 8 hours.

A higher dose of the local anaesthetic will not necessarily produce a longer effect, but a stronger effect may be achieved.

It has been found that the peak blood concentration in a human, following oral administration of the composition of the invention to the human and retention of the composition in the oral cavity of the human until complete dissolution of the composition, is on average from 15 to 45 minutes, preferably 25 to 35 minutes, more preferably about 30 minutes, following the said dissolution.

Indications

The compositions of the present invention are useful in the treatment or alleviation of pain, burning or xerostomia of the oral cavity, pharynx, oral mucosa and pharyngeal mucosa, including oral mucositis. Oral mucositis is a common and often debilitating complication of cancer treatment.

Examples of chemotherapeutic drugs that frequently cause mucositis and/or stomatitis include alkylating agents, for example melphalan and busulphan, antimetabolites, for example cytarabine, floxidine, 5-fluorouracil, mercaptopurine, methotrexate, and thioguanine and cytotoxic drugs, for example, bleomycin, actinomycin D, daunorubicin, cisplatin, etoposide, mytomycin, vinblastine and vincristine. The terms mucositis and stomatitis are often used interchangeably but may include some general distinctions Mucositis describes a toxic inflammatory reaction affecting the gastrointestinal tract, which may result from exposure to chemotherapeutic agents or ionizing radiation Mucositis typically manifests as an erythematous burn-like lesion, or as random focal-to-diffuse lesions. Stomatitis refers to an inflammatory reaction affecting the oral mucosa, with or without ulceration, that may be caused or intensified by pharmacological, particularly chemotherapeutic treatments or by radiotherapy. Stomatitis can range from mild to severe; a patient presenting with severe stomatitis is unable to take anything by mouth.

Accordingly the subject in need of treatment with the compositions according to the invention may be a patient under treatment or having received treatment with any of the above mentioned chemotherapeutic drugs.

The pain, burning or xerostomia may be caused by: Burning Mouth Syndrome or Glossodynia (also known as "Burning tongue" or "Orodynia"), which is a condition characterized by a burning or tingling sensation on the lips, tongue, or entire mouth; Sjögren's syndrome, which is also known as "Mikulicz disease" and "Sicca syndrome"; xerostomia, which is the medical term for the subjective complaint of dry mouth due to a lack of saliva; periodontitis, which is a set of inflammatory diseases affecting the periodontium, i.e., the tissues that surround and support the teeth; toothache, also known as odontalgia or, less frequently, as odontalgy; tonsillectomy, which is a surgical procedure in which the tonsils are removed from either side of the throat; a throat infection or pharyngitis, which is an inflammation of the throat or pharynx; mononucleosis, which is a condition where there is an unusual proliferation of lymphocytes in the blood due to an infection with the Epstein-Barr virus (EBV); or canker sores or aphthous ulcers, which is a type of mouth ulcer and appears as a painful open sore inside the mouth or upper throat characterized by a break in the mucous membrane.

Use of a lozenge increases the salivary secretion. The salivary secretion is activated by taste, chewing and/or tactile stimulation, when the chemoreceptors, periodontal ligamental receptors and nociceptors in the oral mucosa are stimulated. This is an advantage for patients suffering from xerostomia and salivary gland hypofunction, as the increased salivary secretion can reduce discomfort and soreness in the oral cavity and/or pharynx. Furthermore, increased salivary secretion may also contribute to reduced mucosal inflammation and infection.

Particularly for burning mouth syndrome and/or Sjögren's syndrome the lower dosage forms of 5 mg or 10 mg of the local anaesthetic are preferred.

The individual in need of a treatment according to the invention could be any individual; however, preferably, such individual is a human being.

Assessment of pain alleviation may be determined by use of the VAS score. The VAS score is a scale of 0 to 10, wherein 0 is pain free and 10 is the worst imaginable pain. The individual will generally have a VAS score relating to pain of at least 4 to 5, such as at least 6, for example at least 8.

In a further aspect of the invention, the treatment results in a decrease in the severity of symptoms corresponding to a decrease of score as measured according to VAS score herein of at least 15% within 10 minutes, such as least 25%, more preferably of at least 30% in 10 minutes from the start of the treatment. Treatment as used herein means administration of a composition comprising an effective dose of the local anaesthetic. After 30 minutes of treatment the score is preferably decreased by at least 20%, such as at least 30%, for example around 40% to 60%, more preferably at least 40%, yet more preferably at least 50%, even more preferably at least 60% in 30 minutes from the start of the treatment. 1 hour after the start of the treatment preferably results in a decrease of VAS score of at least 30%, preferably at least 40%, more preferably at least 50%, even more preferably at least 55%, yet more preferably at least 60%, even more preferably at least 65%, most preferably at least 70%.

In another embodiment of the invention the compositions may be used to provide anesthesia of the oral cavity, pharynx, oral mucosa and pharyngeal mucosa. In a particular embodiment the anesthesia is provided before diagnostic upper gastrointestinal endoscopy, intubation or dental procedures.

When the anesthesia is to be provided before dental procedures the time spent on said dental procedure may be reduced compared to the time spent without the administration of a composition according to the present invention. It is envisaged that the time spent on the dental procedure may be reduced by at least 2%, such as by at least 5%, for example by at least 7%, such as by at least 10%, such as by at least 12%, for example by at least 15%, for example by at least 17%, such as by at least 20%, for example by at least 25%, such as by at least 30%, for example by at least 35%, such as by at least 40% compared to the time spent without the administration of a composition according to the present invention, after administration of the compositions of the present invention.

In another embodiment of the invention the compositions may be used to provide increased stimulation of saliva. The embodiments where the composition is formulated as a lozenge are particularly useful for this purpose.

The pharmaceutical compositions of the present invention may also be used for a method for achieving sustained release of the local anaesthetic in the mouth or throat over a time period of about from 1 minute, such as from about 2 minutes, for example from about 5 minutes, such as from about 10 minutes, for example from about 15 minutes, such as from about 20 minutes, for example from about 25 minutes, such as from about 30 minutes, for example from about 35 minutes, such as up to about 40 minutes, for example from up to 45 minutes, such as up to about 50 minutes, for example up to about 55 minutes, such as from about 60 minutes, for example from about 70 minutes, such as up to about 80 minutes, for example up to about 90 minutes, such as up to about 100 minutes, for example up to about 2 hours, such as up to about 3 hours, for example up to about 4 hours, such as up to about 5 hours, for example up to about 6 hours. In a preferred embodiment the pharmaceutical compositions of the present invention may also be used for a method for achieving sustained release of a in the mouth or throat over a time period of 1 minute to 30 minutes.

In yet another embodiment of the invention the compositions (even if they do not contain a compound normally recognised as an anti-inflammatory agent, for example if the local anaesthetic is the only active ingredient) may be used to provide an anti-inflammatory effect in the oral cavity, pharynx, oral mucosa and pharyngeal mucosa. Without being bound by theory it is envisaged that compositions of the present invention also have an effect on the inflammatory response. This may be measured by an increase (local or systemic) in state of art biomarkers with anti-inflammatory activity or a decrease in inflammatory biomarkers. The effect on the inflammatory response of bupivacaine or a pharmaceutically active salt hereof is estimated by measuring the level of one or more markers selected from the group consisting of inflammatory markers including but not limited to TNF-α, IL-1, suPAR; anti-inflammatory markers including but not limited to IL-10, IL-4; pain-associated markers including but not limited to IL-6, IL-8, Leukotriene; and acute phase reactants including but not limited to CRP.

The compositions of the invention may be administered in combination with a second treatment, such as in combination with any of the further active ingredients described herein above in the section "Further active ingredient", and the two treatments may be combined to form a kit of parts. The two treatments may be administered simultaneously as separate or combined formulations, or sequentially. Optionally the kits may comprise instructions for use.

Methods for Producing Lozenges

Further aspects of the present invention relates to methods for producing the lozenges described herein above. Any of the lozenges of the present invention may be produced by any methods for producing such known to the skilled person. U.S. Pat. No. 6,194,003, U.S. Pat. No. 5,399,354, WO 2007/110871, WO 2009/042969, WO 2009/042968 and WO 04/070017, for example, describe methods for producing lozenges.

A particular embodiment of the invention relates to a method for producing the compressed powder lozenge of the present invention.

Accordingly a method for producing a compressed powder lozenge may comprise the steps of:
  (a) passing a local anaesthetic as defined, any excipients and optionally a further active ingredient as described herein above described herein above through a sieve,
  (b) mixing the ingredients,
  (c) optionally adding glidant or lubricant and softly mixing with the other excipients,
  (d) compressing the lozenges, each containing a therapeutically effective amount of the local anaesthetic.

A specific method for producing a compressed powder lozenge may comprise the steps of:
  (a) passing a local anaesthetic as defined, filler or binder, non-sweetening agent and aroma, and optionally a further active ingredient as described herein above through a sieve.
  (b) mixing the ingredients,
  (c) adding glidant or lubricant and softly mixing with the other excipients,
  (d) compressing the lozenges, each containing a therapeutically effective amount of the local anaesthetic.

The lozenges are then subjected to a visual check and packed into suitable packaging. One form of suitable packaging is a blister pack of a water-impermeable plastics material (e.g. polyvinylchloride) closed by a metallic e.g. aluminium foil. The patient removes the lozenge by applying pressure to the blister to force the lozenge to rupture and pass through the metal foil seal.

A particular embodiment of the invention relates to a method for producing the compressed granulated lozenge of the present invention.

Accordingly a method for producing a compressed granulated lozenge may comprise the steps of:
  (a) granulating a mixture of a local anaesthetic as defined and any excipients and optionally a further active ingredient to form granules;
  (b) melting a lozenge-forming composition;
  (c) mixing the granules with the molten lozenge-forming composition;
  (d) forming the resulting mixture into lozenges each containing a therapeutically effective amount of the local anaesthetic.

The granulation step may be performed by wet granulation and/or dry granulation. Wet granulation involves the massing of a mix of dry primary powder particles using a granulating fluid. The fluid contains a solvent which must be volatile so that it can be removed by drying, and be non-toxic. Typical liquids include water, ethanol and isopropanol either alone or in combination. The liquid solution can be either aqueous based or solvent based. The dry granulation process is used to form granules without using a liquid solution because the product to be granulated may be sensitive to moisture and heat. Forming granules without moisture requires compacting and densifying the powders. In this process the primary powder particles are aggregated under high pressure.

A specific method for producing a compressed granulated lozenge may comprise the steps of:
  (a) granulating a mixture of a local anaesthetic as defined and optionally a bulking agent with a solution of a binder or a filler and optionally a further active ingredient to form granules;
  (b) melting a lozenge-forming composition comprising non-sweetening agent, aroma and glidant or lubricant;
  (c) mixing the granules with the molten lozenge-forming composition;
  (d) forming the resulting mixture into lozenges each containing a therapeutically effective amount of the local anaesthetic.

Following a wet granulation step, the granulated lozenge-forming composition is preferably heated to a temperature in the range of 110 to 170° C. under vacuum to remove water before the granulated components of the pharmaceutical lozenge formulation are added. The moisture content is preferably less than 2%, more preferably less than 1%. The molten mixture may be passed to individual moulds in which each lozenge is formed or may be drawn into a continuous cylindrical mass from which the individual lozenges are formed. The lozenges are then cooled, subjected to a visual check and packed into suitable packaging. One form of suitable packaging is a blister pack of a water-impermeable plastics material (e.g. polyvinylchloride) closed by a metallic eg aluminium foil. The patient removes the lozenge by applying pressure to the blister to force the lozenge to rupture and pass through the metal foil seal.

A particular embodiment of the invention relates to a method for producing the cast/syrup based lozenge of the present invention.

Accordingly a method for producing a cast syrup-based lozenge may comprise the steps of:
  (a) A base is parboiled to a temperature of 140-160° C. to liquidise the fibre,
  (b) liquidized base is poured out,
  (c) aroma powder is added and kneaded into the base mass until dissolved,
  (d) a local anaesthetic as defined and optionally a further active ingredient is added and kneaded into the base mass until dissolved,
  (e) the mass is added to a cylinder, thereby casting the syrup-based lozenges each containing a therapeutically effective amount of the local anaesthetic.

A specific method for producing a cast or syrup-based lozenge may comprise the steps of:
  (a) sweet soluble dietary fibre containing short chain fructo-oligosaccharides, such as Actilight is parboiled to a temperature of 140-160° C. to liquidise the fibre,
  (b) liquidized fibre is poured out,
  (c) aroma powder is added and kneaded into the fibre mass until dissolved,
  (d) a local anaesthetic as defined is added and kneaded into the fibre mass until dissolved,
  (e) adding the mass to a cylinder, thereby casting the syrup-based lozenges each containing a therapeutically effective amount of the local anaesthetic.

The lozenge-forming composition is preferably heated to a temperature in the range of 110 to 170° C., preferably 140 to 160° C. All excipients are preferably added prior to the addition of bupivacaine or a pharmaceutically active salt hereof. The composition is then weighed and the amount of the local anaesthetic needed to produce lozenges with the desired amount of the local anaesthetic is calculated based on the mass of the base and added thereto. Preferably the composition is cooled to about 110 to 130° C., such as 120° C. before the addition of the local anaesthetic and optionally a further active ingredient.

Packaging

The compositions so prepared are individually packaged in a manner that promotes shelf life and maximizes the stability of the local anaesthetic. These requirements translate into a package design in which both the air space and exposed surface area of the composition, preferably a lozenge are minimized, and in which the packaging material used has very low permeability to vapor. A plastic-lined foil, wherein the plastic is a low permeability material, is optimal. Ideally, the packaging material should be in contact with at least 85% of the surface of the composition, preferably a lozenge to minimize loss of flavor, and packaging materials that do not transmit organic vapors are optimal. For example, polyolefinic materials such as poly(vinylidene chloride), polyethylene (including low density and higher density polyethylenes), polypropylene, and copolymers thereof represent suitable packaging materials.

The composition, preferably a lozenge, of the invention may be prepared in any number of shapes and sizes, and the invention is not limited in this regard. Different shapes and sizes may be desirable for different applications. Typical dimensions, however, are on the order of 0.4"×0.5"×0.2" (10×13×5 mm) for lozenges, while lozenge weight is generally in the range of about 0.4 to 1.8 g, preferably around 0.7 g for compressed powder and granulated lozenges and in the range of about 0.5 to 10 g, such as 1 to 8 g, for example 2 to 7 g, preferably 2.5 to 5.5 g for the cast or syrup-based lozenges. The diameter of the lozenge is typically in the range from 5 to 30 mm, such as from 8 to 25 mm, for example from 10 to 20 mm, preferably around 12 mm.

REFERENCES

T. Hung, V. Moore-Gillon, J. Hem, A. Hinton, N. Patel, 2002, Topical bupivacaine in paediatric day-case tonsillectomy: a prospective randomized controlled trial. The Journal of Laryngology & Otology, Vol. 116, pp. 33-36.

EXAMPLES

Example 1: Lozenges

Lozenges are prepared from casting (lozenge) or from compression (compressed lozenge).
Compressed Lozenge, Powder Base (5 mg, 10 mg, 25 mg):

| Compressed lozenge, 25 mg bupivacaine, liquorice | | |
|---|---|---|
| Ingredients | Specification | Amount (mg)/1 tablet |
| Bupivacaine hydrochloride | Ph. Eur | 28.16 mg |
| Perlitol SD 200 | Ph. Eur | 523.48 mg |
| Talcum | Ph. Eur | 34.61 mg |
| Magnesium stearate | Ph. Eur | 3.75 mg |
| Aspartame | Ph. Eur | 10.0 mg |
| Liquorice powder | DLS 86 | 100.0 mg |
| | | 700 mg |

| Compressed lozenge, 10 mg bupivacaine, liquorice | | |
|---|---|---|
| Ingredients | Specification | Amount (mg)/1 tablet |
| Bupivacaine hydrochloride | Ph. Eur | 11.26 mg |
| Perlitol SD 200 | Ph. Eur | 540.38 mg |
| Talcum | Ph. Eur | 34.61 mg |
| Magnesium stearate | Ph. Eur | 3.75 mg |
| Aspartame | Ph. Eur | 10.0 mg |
| Liquorice powder | DLS 86 | 100.0 mg |
| | | 700 mg |

| Compressed lozenge, 5 mg bupivacaine, liquorice | | |
|---|---|---|
| Ingredients | Specification | Amount (mg)/1 tablet |
| Bupivacaine hydrochloride | Ph. Eur | 5.63 mg |
| Perlitol SD 200 | Ph. Eur | 546.01 mg |
| Talcum | Ph. Eur | 34.61 mg |
| Magnesium stearate | Ph. Eur | 3.75 mg |
| Aspartame | Ph. Eur | 10.0 mg |
| Liquorice powder | DLS 86 | 100.0 mg |
| | | 700 mg |

To prepare a compressed lozenge, bupivacaine hydrochloride, perlitol, talcum, magnesium stearate, aspartame and liquorice powder were passed through a 180-mesh sieve prior to weighing. Bupivacaine hydrochloride, perlitol, aspartame and liquorice powder were mixed together and thereafter magnesium stearate with talcum were added and softly mixed with the other excipients. The lozenges were produced using direct compression with Korsch PH106—6 Station EU and a stamp with diameter: 12 mm, interval from 8-25 mm to give lozenges weighing approximately 0.7 g, range from 0.4-1.8 g, with a round, domed shape.

| Lozenge, syrup base (25 mg) each lozenge weighing approximately 5.5 grams | | |
|---|---|---|
| Ingredients | Specification | |
| Bupivacaine hydrochloride | Ph. Eur | 110 g |
| Actilight 950 S | | 20 Kg |
| Cocoa powder 20-22% | | 1.5 Kg |

1. Actilight was measured and poured into a clean steel pot which was free of rust,
2. Actilight was parboiled to a temperature of 140-160 degrees Celsius to liquidise the fibre,
3. Liquidized Actilight was poured out onto a production table, which was a massive cast iron table with built-in water cooling. Paraffin oil was applied to the table prior to pouring the actilight to ensure the actilight could be loosened from the table. The oil evaporates at the high temperatures and does not penetrate into the mass,
4. The temperature had fallen to 120 degrees Celsius,
5. Cocoa powder was sprinkled onto the mass and then kneaded into the actilight mass until fully dissolved,
6. The mass was weighed in order to calculate the amount of Bupivacaine to be added,
7. Bupivacaine was added and kneaded into the actilight mass until dissolved, then kneaded for an additional five minutes to ensure it is fully dissolved,
8. The mass was then added to a cylinder, thereby casting the syrup based lozenges,
9. All lozenges not having the desired shape or size, such as the end-pieces, was discarded,
10. The lozenges were then placed in a sieve whereby sharp edges were removed,
11. The weight of the lozenges were controlled,
12. The lozenges were then packaged.
The lozenges comprised 25 mg per lozenge and weighed between 2.5-5.5 gram each.

Example 2: Phase One Trials with Bupivacaine Lozenge

Bupivacaine has not been used as local oral administration before. Therefore it is important to investigate the plasma concentrations after topical oral administration of a compressed lozenge containing up to 50 mg bupivacaine, to show that the concentration will not reach a toxic level, both as a single dose and multiple doses.

The purpose of this study is to investigate the pharmacokinetics of bupivacaine after topical oral administration. The plasma concentration of bupivacaine is measured after absorption over an intact oral mucosa after administration of a compressed lozenge containing respectively 5, 10, 25 and 50 mg bupivacaine as a single dose and 25 mg as multiple doses.

These are prospective, descriptive studies. The subjects were ten healthy young males. Samples of full blood were taken in lithium-heparin pipes for anticoagulant effect. After the blood sample is collected it is centrifuged at 2500 rounds per minute for 15 minutes at 4° C. Approximately 1 ml plasma is taken from the sample and put into vials and right away put into a −80° C. freezer, where it is kept until analysis.

Study I: Single Dose Kinetics

The aim of the study was to investigate the pharmacokinetics of bupivacaine by topical oral administration. The concentration of bupivacaine was measured in the blood after absorption from an intact oral mucosa after administration of a compressed lozenge containing respectively 5, 10 or 25 mg of bupivacaine. On study days 1, 2, 3 and 4 (interspersed with single wash-out days) the subjects were given one 5 mg lozenge, one 10 mg lozenge, one 25 mg lozenge or two 25 mg lozenges, respectively.

All subjects had a peripheral venous catheter (PVC), from which the blood was drawn. Before the study began, the subjects drank 250 ml water to remove any traces of coffee, cola or other potential absorption enhancers. After 10 minutes a compressed lozenge was administered. The subjects had to suck the lozenge until it was completely dissolved. A baseline blood sample was taken, the lozenge was administered and then blood samples were taken at 0 min (i.e. when the lozenge has completely dissolved in the mouth, 15 min, 30 min, 45 min, 60 min, 75 min, 90 min, 105 min, 120 min, 150 min, 180 min, 210 min, 240 min, 270 min, 300 min, 330 min and 360 min.

The maximum dosage administered was 50 mg, which resulted in a maximum bupivacaine plasma concentration of less than 600 ng/ml (FIG. 1). This is well below the toxic level in man of 2-4 µg/ml, All the healthy subjects felt the anesthetic effect after receiving 5 mg and 10 mg bupivacaine and none of them felt any discomfort. After receiving 25 mg some of the subjects felt discomfort especially in the pharynx because of the increased anesthetic effect. The discomfort was further increased after receiving the dose of 50 mg bupivacaine. None of the subjects experienced any side effects.

Study II: Multiple Doses Kinetics

The multiple doses study was conducted over 72 hours consecutively, where the subjects were administrated a lozenge containing 25 mg of bupivacaine four times a day in the awake hours.

The aim of the study was to measure the concentration of bupivacaine in the blood after absorption from an intact oral mucosa after administration of a lozenge containing 25 mg of bupivacaine given four times a day. The idea of administrating the lozenge four times a day around specific hours was to create a study that was comparable to a patient that would need pain relief in the awake hours and especially before eating. Therefore the lozenges were administered at 8 am, 12 am, 6 pm and 10 pm, to give a total daily dose of 100 mg bupivacaine.

The subjects drank 250 ml water to remove any traces of coffee, cola or other potential absorption enhancers. After 10 minutes a compressed lozenge was administered. The subjects had to suck the lozenge until it was completely dissolved. A baseline blood sample was taken, lozenges were administered at the following times: 8 am, 12 am, 6 pm, and 10 pm, and blood samples were taken 30 minutes after each administration.

Figure 2:
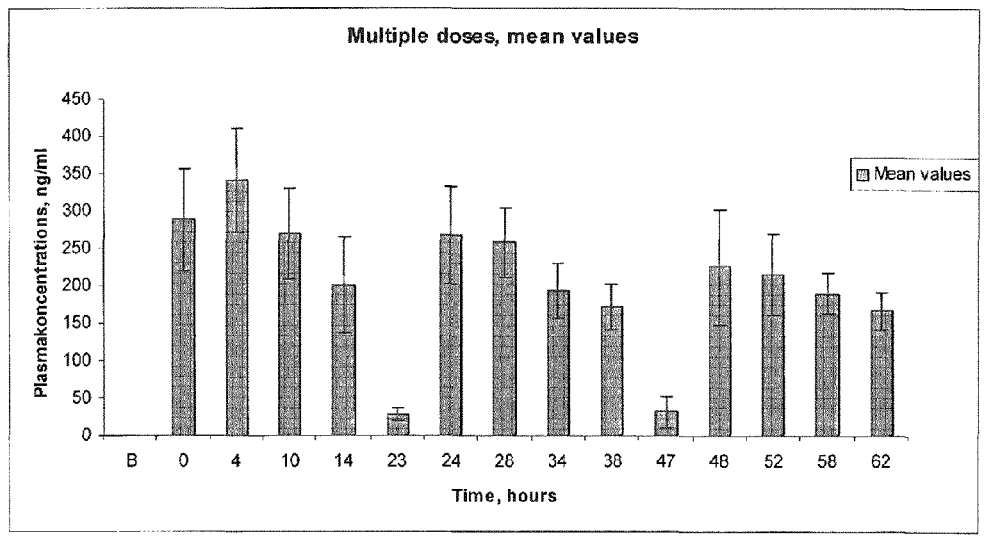
FIG. 2 shows the plasma concentrations from a multiple dose study (Example 2, Study II). "B" and the values at 23 h and 47 h are baseline samples.

Results:

The peak plasma concentrations are lower than the toxic level. Furthermore there is a decrease in the plasma concentrations between every administration of the lozenge, which shows that bupivacaine is not being accumulated in the body (FIG. 2), either with respect to peak nor to the lowest value at time points 23 and 47 hours.

Study III—Inflammation

The aim of the study was to analyze blood and saliva before and after the administration of a bupivacaine lozenge, to get basic information in order to investigate the hypothesis that bupivacaine has an anti-inflammatory effect and to see if the effect can be detected by a change of the concentration in inflammation and pain markers.

This phase one trial in healthy subjects is designed to be used as a control for patients who have an inflammatory disease, so we did not expect to see any major changes, as the subjects are without inflammation.

All the subjects had their blood and saliva sample taken at baseline as well as 30 minutes after administration of the lozenge at times 8 am, 12 am, 6 pm and 10 pm.

Results:

We were able to measure the inflammation marker MCP1. As the concentration of MCP1 is low (no inflammation in healthy subject) there was no difference in the concentration after the bupivacaine lozenge was administered.

Study IV: Aspiration Study

Other studies have shown that the feeling in the pharynx will be reduced after administration of lidocaine and that it can affect the normal self-regulating swallowing reflex. Since the bupivacaine lozenge is for oral use, we needed to test the swallowing reflex to prove that the lozenge can be used as pain relief before mealtimes without the risk of aspiration.

The subjects had to be fasting for 3 hours before the examination. They were all given a compressed lozenge containing 25 mg bupivacaine and were told to suck the lozenge until it was completely dissolved. The subjects then had to take a mouthful of barium-contrast fluid. The path of the fluid through the esophagus was recorded using video radiography (radiation dose <0.35 mSv), which was then analyzed for aspiration. The examination is a standard examination for patients with swallowing problems.

Results:

None of the 10 subjects showed any signs of aspiration on the radiography.

Study V—Dose Response

The aim of the study was to investigate the effect of local anesthesia after oral administration of a lozenge containing respectively 10 and 25 mg of bupivacaine.

When the lozenge was fully dissolved in the mouth the healthy subjects had to assess their feeling of anesthesia on a Visual Analogue Scale (VAS). They assessed the feeling at different places in the mouth, rear, middle and front of the tongue, the upper and lower lip, right and left cheek and the pharynx. The assessments were done every 15 minutes for 90 minutes.

Figure 3:
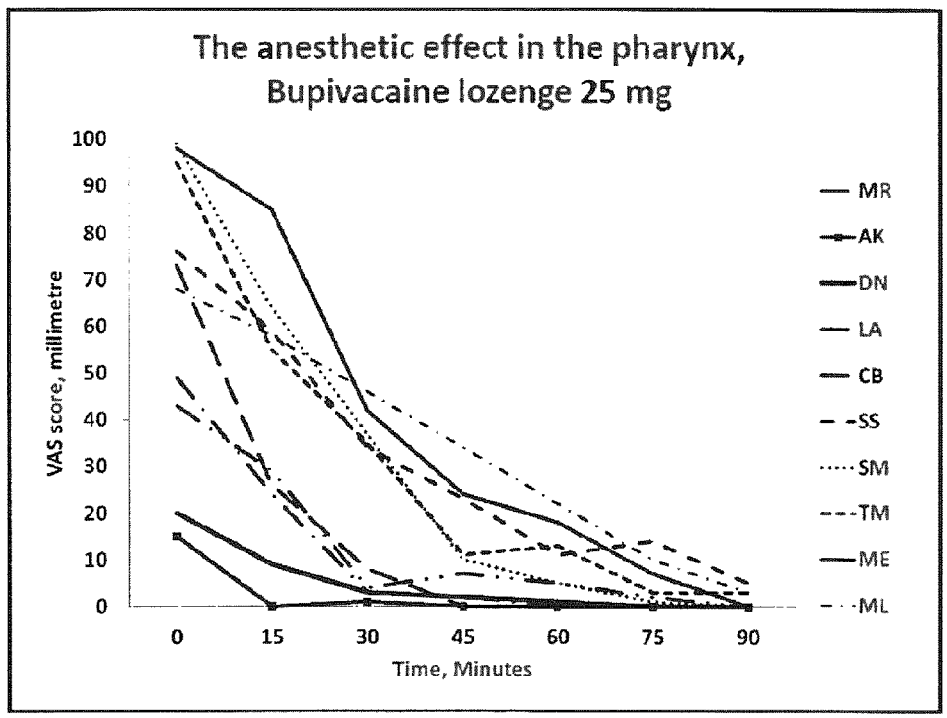
FIG. 3 shows the VAS assessments for the pharynx after administration of a 25 mg bupivacaine lozenge (Example 2, Study V).

Results:

After receiving a 25 mg bupivacaine lozenge, all the healthy subjects felt that they were anesthetized in the pharynx and the effect lasted for approximately 30 minutes (FIG. 3). The same tendency was seen for the assessment of the middle of the tongue as all the subjects felt the anesthesia and the effect lasted for approximately 30 minutes.

Study VI—Blood Pressure and Telemetry

Hypertension and hypotension are categorized as respectively a very common and a common side effect to bupivacaine, while arrhythmia is a rare side effect. All the subjects had their blood pressure measured and telemetry was performed for 24 hours. The subjects were given a lozenge containing 25 mg of bupivacaine. The blood pressure and telemetry measurements continued for the next 24 hours. The blood pressure was measured at the same time both days. The first two hours it was measured every 15 minutes, the next two hours every 30 minutes, and during the last 20 hours every hour.

The aim of the study was to demonstrate that these side effects do not occur by administration of a bupivacaine lozenge containing 25 mg. The study will monitor the blood pressure as well as telemetry for 48 hours.

Results:

The lozenge had no effect on the blood pressure or the heart rate

Study VII: Single Dose Kinetics, Fasting

The single dose kinetics was conducted over 10 hours. The subjects had been fasting from 12 pm the night before the study began. The subjects were administrated a compressed lozenge containing 25 mg of bupivacaine. The blood collection began at approximately 7 am.

In our previous results we have seen an extra peak. The aim of this study was to investigate if the extra peak was from gastrointestinal absorption.

Procedure for Blood Sample Collection for the Study:

Baseline blood sample. Administration of lozenge. Blood sample at the following times: 0 min, 15 min, 30 min, 45 min, 60 min, 75 min, 90 min, 105 min, 120 min, 150 min, 180 min, 210 min, 240 min, 300 min, 360 min, 420 min, 480 min, 540 min and 600 min. (Time 0 minutes is when the lozenge is completely dissolved in the mouth.)

Figure 4:
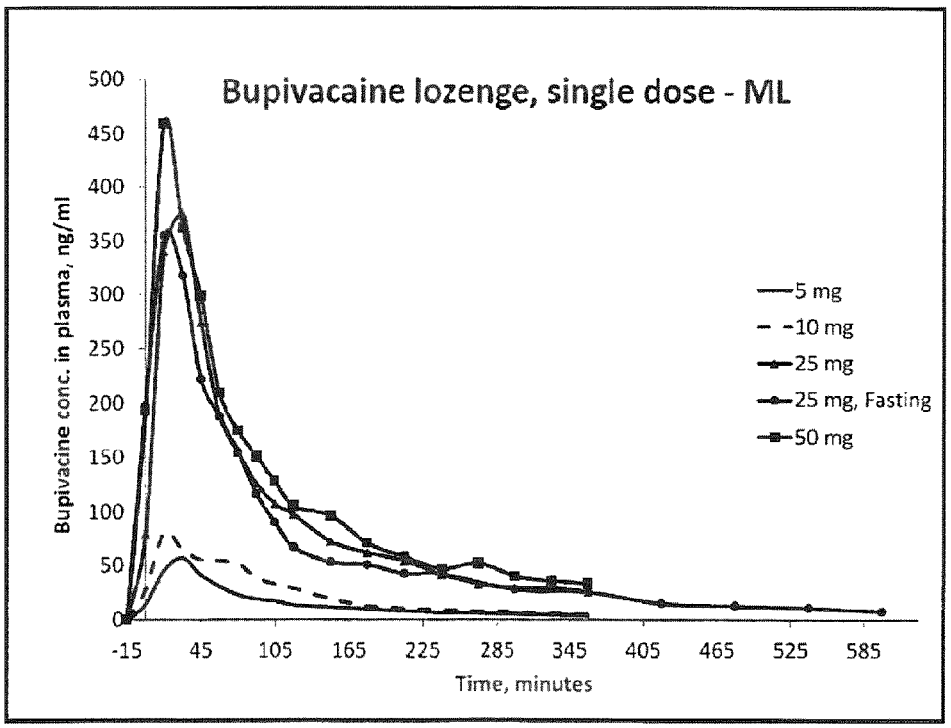
FIG. 4 shows the plasma level in a single patient given various doses of bupivacaine, and demonstrates that fasting does not affect the plasma level (Example 2, Study VII).

Results:

The fasting did not influence the results. In FIG. 4 the results are shown from ML, which is one of the ten healthy subjects. The results from 25 mg and 25 mg fasting are almost identical.

Pilot Study Aarhus—Kinetics, Non-Intact Mucosa

The study was conducted over 2-3 hours on three patients from Aarhus University hospital. The patients were suffering from head or neck cancer with stage 3 mucositis with a non-intact oral mucosa. The aim of the study was to investigate the pharmacokinetics of bupivacaine by topical oral administration of a 25 mg lozenge. A baseline blood sample was taken, followed by administration of the lozenge, and then blood samples were taken at 0 min (i.e. when the lozenge is completely dissolved in the mouth), 15 min, 30 min, 45 min, 60 min, 75 min, 90 min, 105 min, 120 min, 150 min and 180 min.

Figure 5:
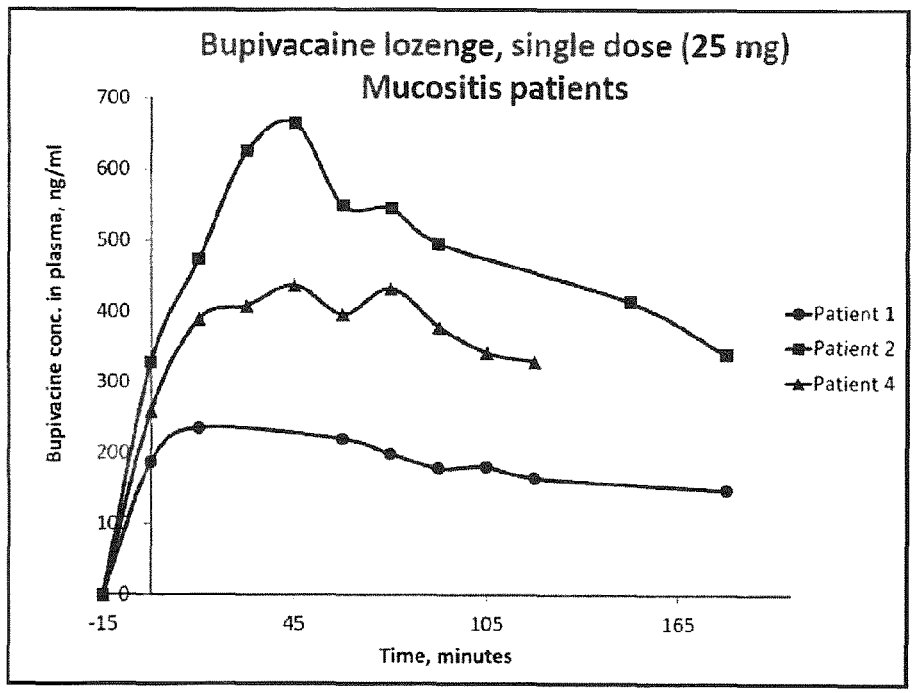
FIG. 5 shows serum concentrations of bupivacaine in three patients with non-intact oral mucosa (Example 2, Pilot Study Aarhus).

Results:

The maximum plasma concentration of bupivacaine was below 700 ng/ml, which is below the toxic level (FIG. 5).

Pilot Study I, II, III, IV Kinetics

Pilot Study I:

One subject swallowed an intact lozenge containing 25 mg of bupivacaine. The aim was to investigate the gastrointestinal absorption, as the oral mucosal absorption will be eliminated.

Pilot Study II:

One subject sucked on a lozenge containing 25 mg of bupivacaine until it was completely dissolved. The aim was to investigate the oral absorption within smaller time intervals than the previous studies.

Pilot Study III:

One subject gargled a solution of 25 mg bupivacaine dissolved in 20 ml water. After 5 minutes the solution was spat out. The aim was to investigate the kinetics when a known dose of bupivacaine in a solution is absorbed only over the oral mucosa.

Pilot Study IV:

One subject gargled a solution of a dissolved lozenge containing 25 mg of bupivacaine in 20 ml water and spat it out after 10 minutes. The aim was to investigate the kinetics when a known dose of bupivacaine in a solution is absorbed only over the oral mucosa.

The study was conducted over two hours on four healthy subjects. The subjects had been fasting for 3 hours before the study began. The blood collection began as soon as the lozenge was given to the subjects, giving a baseline blood sample, followed by administration of lozenge and then blood sampling at the following times: 0 min (i.e. when the subject was given the lozenge or solution), 2 min, 4 min, 6 min, 8 min, 10 min, 12 min, 14 min, 16 min, 20 min, 25 min, 30 min, 35 min, 40 min, 45 min, 50 min, 55 min, 60 min, 70 min, 80 min, 90 min, 100 min, 110 min and 120 min.

Figure 6:
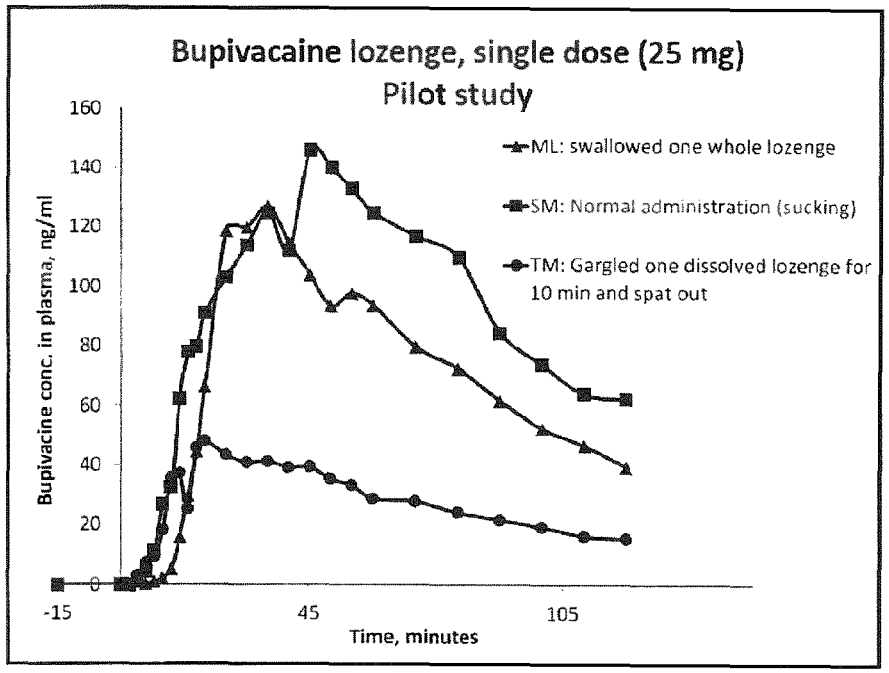
FIG. 6 compares plasma levels in patients who either swallowed, sucked or gargled with the lozenge (Example 2, Pilot Study kinetics).

The subjects in study I and II showed no signs of discomfort during the study. In study III the subject felt the anesthetic feeling in the mouth to be very uncomfortable. While gargling the solution, the subject in study III and IV felt it hard to keep the solution in the mouth because of the severe anesthetic feeling. The subject felt that the solution caused an increased and unpleasant anesthetic feeling compared to the lozenge and the effect was not lasting as long as the lozenge. In FIG. 6 the plasma concentrations of bupivacaine are shown from studies I, II and IV. It is seen that the systemic absorption is low when a lozenge is swallowed and even lower when a dissolved lozenge is gargled and not swallowed.

Example 3: Patient Cases

Four patients with head and neck cancer received one lozenge containing 25 mg bupivacaine. Before and after administration of the lozenge the patient assessed VAS score for pain in the mouth and pharynx and completed a non-validated questionnaire.

Patient Case 1:

64-year-old male. Recently started chemotherapy. Current pain medication: acetaminophen (paracetamol) 500 mg per tablet as required. In the past week the patient had experienced a slight pain in the mouth and pharynx, and suffered from dryness in the mouth. He had no trouble eating, swallowing or enjoying food.

The patient received one lozenge with the taste of liquorice-menthol. The treatment was discontinued after a couple of minutes due to discomfort when swallowing. The patient had lost most of his sense of taste due to the disease, but still he found the taste and the texture of the lozenge to be good.

The patient's VAS score before administration of the lozenge was 0 for pain in the mouth and 0.6 for pain in the pharynx. There was no change in the VAS score after administration of the lozenge, but the patient reported that the lozenge decreased the dryness in his mouth, due to increased saliva.

Patient Case 2:

65-year-old male. He had received six weeks of chemotherapy. Current pain medication: acetaminophen (paracetamol) 500 mg per tablet as required. In the past week the patient had experienced slight pain in the mouth and pharynx. He also experienced slight dryness in the mouth and had problems with adhesive saliva. The patient had trouble eating, and he found it hard to enjoy food. Therefore nutrition was supplied through a stomach tube. The patient received one lozenge with the taste of banana. He found the taste and texture of the lozenge to be good.

The VAS score before administration of the lozenge was 0 for pain in the mouth and 2.5 for pain in the pharynx. After the administration there was no change in the VAS score for the mouth. However, a reduction to 1.5 (i.e. a decrease of 40%) on the VAS score of the pharynx was observed.

The lozenge induced no discomfort in the mouth but the patient felt some discomfort during swallowing.

Patient Case 3:

59-year-old male. He had received six weeks of chemotherapy. Current pain medication: morphine 4 times a day and acetaminophen (paracetamol) 500 mg per tablet 8 times a day. In the past week the patient had experienced pain in the mouth and pharynx. Furthermore he had been very sore and dry in the mouth and suffered from adhesive saliva. He also experienced pain in the jaw, which resulted in difficulty opening the mouth, and swallowing solid food, and made it difficult for the patient to enjoy food.

The patient received one lozenge with the taste of cacao. The treatment was discontinued after a couple of minutes due to discomfort when swallowing. He found the taste of the lozenge to be bitter, but the texture of the lozenge to be good.

The patients VAS score before administration of the lozenge was 0 for pain in the mouth and 5.8 for pain in the pharynx. The VAS score after administration of the lozenge was unchanged for pain in the mouth. However, the patient experienced a reduction in pain in the pharynx where the score was reduced by almost half (47%) to 3.1. The patient found the rapid effect of the lozenge beneficial compared to morphine, but he experienced insufficient pain relief, and desired more anesthetics to decrease his pain.

Patient Case 4:

69-year-old male. Current pain medication: 2×acetaminophen (paracetamol) 500 mg per tablet 4 times a day. In the past week the patient had experienced pain in the mouth and pharynx. He was sore in the mouth and had pain in the jaw. The patient experienced difficulty opening the mouth and had problems swallowing both solid and mashed food, which made it difficult to enjoy food. Furthermore he constantly had a feeling of a lump in the throat. He experienced dryness in the mouth and suffered from adhesive saliva.

The patient received one lozenge with the taste of liquorice-menthol. The treatment was discontinued after a short period of time due to discomfort in both in the mouth and during swallowing. The patient found the taste of the lozenge to be bitter, but the texture of the lozenge to be good.

The patient's VAS score before administration of the lozenge was 3 for pain in the mouth and 5 for pain in the pharynx. The VAS score after administration of the lozenge was unchanged for pain in the mouth. The patient experienced a reduction in pain in the pharynx and the score was reduced by half to 2.5. Furthermore, the patient felt that the lump in his throat was gone after administration of the lozenge.

Mucositis patient case 5: The patient was a 51-year-old female, currently in radiation treatment and hospitalized due to training in how to use a feeding tube. Current pain medication: Contalgin 20 mg two times a day (8 am and 8 pm) and morphine 10 mg every $4^{th}$ hour. In the past week the patient had experienced a lot of pain in the mouth and pharynx. Furthermore she had been very sore and dry in the mouth and had suffered from adhesive saliva. She could not swallow solid food, so she had a feeding tube.

The patient received one compressed lozenge with the taste of liquorice. The patient's VAS score before administration of the lozenge was 2 for both pain in the mouth and for pain in the pharynx. The VAS score after administration of the lozenge was unchanged, but the administration of morphine was postponed for 2 hours. She would normally take a dose of morphine at 10 am, but got the lozenge instead and therefore she did not need the morphine before 12 am. The lozenge induced no discomfort in the mouth or during swallowing. She liked the taste and consistent of the lozenge and would use it as pain relief.

Example 4: Patient Cases

Two pilot studies with respectively a Burning Mouth Syndrome patient and a Sjögren's syndrome patient was performed at the Department of Odontology, University of Copenhagen. Both patients received a lozenge and filled in a questionnaire and assessed VAS for pain and dryness before and after the administration of the lozenge.

Patient Case Burning Mouth Syndrome

The patient was an 84-year-old female. Generally she evaluated her own health as good and was not taking any kind of medicine. The patient was recently diagnosed with Burning Mouth Syndrome. She suffered from a burning sensation on the tip and on both sides of the tongue and experienced a decreased sensation of taste and a taste of metal. The patient also suffered from dryness of the mouth, and because of these symptoms the patient sometimes found it difficult to talk. The patient had suffered from these symptoms for the last 6 months, and the symptoms occurred abruptly and without any causal explanation.

The patient received one lozenge containing 5 mg of bupivacaine with the taste of liquorice. It took the patient approximately 20 minutes to dissolve the lozenge in her mouth.

The patient's VAS before administration of the lozenge was 5 for burning/pain in the mouth, 0 for burning/pain in the throat and 3 for dryness in the mouth. After the administration, VAS was decreased to 4 for burning/pain in the mouth (i.e. a reduction of 20%), was unchanged for burning/pain in the throat and was increased to 5 for dryness in the mouth. The reason for the patient's experience of increase in dryness might be explained by the patient's decreased sensation of taste, which can be expressed as an increased dryness. Changing the taste of the lozenge to a fruity flavor might solve this problem. Besides that, the patient found the taste and texture of the lozenge as good. The patient was satisfied with the anesthetic effect of the lozenge and would use it as an anesthetic treatment.

Patient Case Sjögren's Syndrome

The patient was a 43-year-old female. Generally she evaluated her own health as good and was not taking any kind of medicine. The patient was diagnosed with Sjögren's syndrome one year ago. She had suffered from pain on the tip of her tongue and experienced an altered taste sensation and a taste of salt. The patient also suffered from dryness of the mouth, which sometimes made it difficult for her chew. On the day of the pilot study she had a throat infection and for that reason suffered from a sore throat.

The patient received one lozenge containing 5 mg of bupivacaine with the taste of liquorice. It took the patient approximately 35 minutes to dissolve the lozenge in her mouth.

The patient's VAS before the administration of the lozenge was 1.5 for pain in the mouth, 4 for pain in the throat (throat infection) and 2 for dryness of the mouth. After the administration VAS was decreased to 0.5 for pain in the mouth (a decrease of 66%), 1 for pain in the throat (a decrease of 75%) and 1 for dryness of the mouth (a decrease of 50%). The patient assessed the taste and texture of the lozenge as good and the patient was satisfied with the anesthetic effect of the lozenge and would use it as an anesthetic treatment.

Example 5: Patient Cases

Gastrointestinal Endoscopy

Four patients have been included in the study so far. Two patients received the bupivacaine lozenge and two patients the Xylocaine® (lidocaine) spray. The nurse who has been present during all four examinations stated that she thinks the endoscopy looks more pleasant for the patients receiving the lozenge. The results have not yet been analyzed formally.

Example 6: Evaluation of the Effect of Different Anaesthetic Formulations

Method—Baseline capsaicin: A 0.25% capsaicin solution was given on the first day of the trial, before the other five trials with capsaicin. The healthy subjects gargled 5 ml solution of capsaicin for 1 min. and swallowed the solution. VAS assessment of pain at different locations in the mouth was done when they swallowed the solution and afterwards every 10 min. for one hour. 0 was no pain and 100 was maximum pain.

Method—Bupivacaine lozenges: There was one day between the administration of the bupivacaine lozenge and the bupivacaine cast lozenge. The healthy subjects received one 25 mg bupivacaine lozenge on the first day of the trial and one 25 mg bupivacaine cast lozenge on the second day. When the lozenge was fully dissolved in the mouth the subjects gargled a 0.25% capsaicin solution for 1 minute and spat it out. Straight after, a VAS assessment of pain was done, where 0 was no pain and 100 was maximum pain. The VAS assessments were done every 10 minutes for one hour.

Method—Lidocaine anaesthetics: The six healthy subjects were grouped two and two so that each group received the lidocaine spray, solution and lozenge in different order. There was two hours between each of the three administrations of the lidocaine anaesthetics.

In the first administration, the subjects were sprayed 10 times in the mouth, which was equivalent to 100 mg lidocaine (standard treatment in the clinic is 2-3 sprays). They gargled the solution for 1 minute and swallowed it. In the second administration, the subjects received 5 ml of a lidocaine solution, which was equivalent to 100 mg lidocaine. They gargled the solution for 1 minute and swallowed it. In the third administration the subjects received one 100 mg lidocaine lozenge. When the lozenge was fully dissolved in the mouth (or immediately after the lidocaine solution was swallowed, in the first and second administrations) the subjects gargled a 0.25% solution of capsaicin for 1 min. and spat it out. Straight afterwards, a VAS assessment on pain was done, where 0 was no pain and 100 was maximum pain. The VAS assessments were done every 10 minutes for one hour. The results from 0 to 30 minutes are shown in Table 2. Two subjects had to be with withdrawn as one subject experienced severe discomfort when he received the capsaicin solution, and the other subject misunderstood the VAS and therefore the results were unusable.

TABLE 2

| | Capsaicin (Mean VAS) | | | | | | | | | | | | | | | | | | | | | | | |
|---|---|---|---|---|---|---|---|---|---|---|---|---|---|---|---|---|---|---|---|---|---|---|---|---|
| | Mid tongue | | | | Upper lip | | | | Lower lip | | | | Right cheek | | | | Left cheek | | | | Pharynx | | | |
| N = 4 subjects | 0 | 10 | 20 | 30 | 0 | 10 | 20 | 30 | 0 | 10 | 20 | 30 | 0 | 10 | 20 | 30 | 0 | 10 | 20 | 30 | 0 | 10 | 20 | 30 |
| Bupivacaine lozenge | 50 | 25 | 7 | 2 | 26 | 18 | 5 | 2 | 18 | 12 | 2 | 2 | 20 | 9 | 3 | 2 | 21 | 8 | 3 | 1 | 44 | 20 | 18 | 4 |
| Bupivacaine Cast lozenge | 75 | 44 | 18 | 7 | 56 | 27 | 10 | 3 | 57 | 27 | 8 | 1 | 52 | 27 | 8 | 0 | 58 | 28 | 16 | 0 | 51 | 28 | 14 | 4 |
| Lidocaine lozenge | 63 | 31 | 17 | 5 | 50 | 41 | 15 | 2 | 46 | 40 | 17 | 5 | 34 | 34 | 14 | 6 | 34 | 33 | 14 | 4 | 33 | 22 | 5 | 3 |
| Lidocaine spray | 53 | 68 | 29 | 15 | 36 | 47 | 13 | 10 | 39 | 47 | 13 | 10 | 45 | 53 | 19 | 13 | 53 | 54 | 16 | 13 | 52 | 38 | 18 | 15 |
| Lidocaine Solution | 60 | 38 | 14 | 3 | 24 | 26 | 9 | 8 | 23 | 28 | 7 | 4 | 33 | 34 | 11 | 3 | 34 | 34 | 12 | 3 | 24 | 24 | 10 | 3 |
| Baseline Capsaicin | 67 | 42 | 15 | 4 | 40 | 18 | 8 | 2 | 40 | 17 | 8 | 2 | 44 | 22 | 14 | 2 | 45 | 22 | 9 | 2 | 54 | 39 | 18 | 9 |

The bupivacaine compressed lozenge had consistently the best effect (i.e. the subjects had the lowest VAS score) in terms of pain on the mid-tongue, upper and lower lips, and right and left cheeks. Only in relation to the pharynx did another treatment perform better, namely the lidocaine lozenge over most of the 30 minute period (with the lidocaine solution doing best in the first 8 minutes or so).

The invention claimed is:

1. A method for the treatment of pain associated with oral mucositis in a subject undergoing treatment for cancer comprising locally administering to the mouth or throat of the subject a sustained-release composition in the form of a lozenge comprising an active ingredient consisting of bupivacaine or a salt thereof.

2. The method of claim 1, wherein the active ingredient is a hydrochloride salt of bupivacaine.

3. The method of claim 1, wherein the bupivacaine or salt thereof is present in an amount of 0.1 to 75 mg per lozenge.

4. The method of claim 1, wherein the bupivacaine or salt thereof is present in an amount of 3 to 75 mg per lozenge.

5. The method of claim 1, wherein the lozenge is formulated to provide sustained release of the bupivacaine salt thereof over a time period of at least 20 minutes.

6. The method of claim 5, wherein the lozenge is formulated to provide sustained release of the bupivacaine salt thereof over a time period of 20 minutes to about 6 hours.

7. The method of claim 1, wherein the peak blood concentration in a human, following oral administration of the lozenge to the human and retention of the lozenge in the oral cavity of the human until complete dissolution of the lozenge, is on average from 15 to 45 minutes, following the said dissolution.

8. The method of claim 1, wherein the lozenge includes an applicator.

9. The method of claim 1, wherein the lozenge is selected from the group consisting of powder-based lozenges, syrup-based lozenges and granulated lozenges.

10. The method of claim 1, wherein the lozenge comprises 0.1-5% (w/w) of the bupivacaine or salt thereof, 70-85% (w/w) of a filler or a binder, 0-10% (w/w) of a glidant or a lubricant, 0.5-5% (w/w) of a non-sugar sweetening agent, and 5-20% (w/w) of an aroma compound.

11. The method of claim 1, wherein the lozenge comprises 0.01-5% (w/w) of the bupivacaine or salt thereof, 70-95% (w/w) of a base, and 3-20% (w/w) of an aroma compound.

12. The method of claim 1, wherein the lozenge is administered for the treatment of pain of the oral cavity, pharynx, oral mucosa or pharyngeal mucosa.

13. The method of claim 12, wherein the treatment results in a decrease in severity of symptoms corresponding to a decrease of score as measured according to the VAS score of at least 15% within 10 minutes from start of the treatment and/or at least 20% after 30 minutes of treatment and/or at least 30% 1 hour after the start of the treatment.

14. A method for the treatment of pain associated with oral mucositis in a subject undergoing treatment for cancer comprising locally administering to the mouth or throat of the subject a sustained-release composition in the form of a lozenge, wherein the sustained-release composition comprises an active ingredient consisting of bupivacaine or a salt thereof and the sustained-release composition is capable of completely dissolving.

15. The method of claim 14, wherein the bupivacaine or salt thereof is present in an amount of 3 to 75 mg per lozenge.

16. The method of claim 14, wherein the sustained-release composition comprises a hydrochloride salt of bupivacaine.

17. The method of claim 14, wherein the lozenge includes an applicator.

18. The method of claim 14, wherein the lozenge is selected from the group consisting of powder-based lozenges, syrup-based lozenges and granulated lozenges.

19. The method of claim 14, wherein the lozenge is formulated to provide sustained release of the bupivacaine or salt thereof over a time period of at least 20 minutes.

20. The method of claim 14, wherein the sustained-release composition does not contain ethyl cellulose.

21. The method of claim 14, further comprising a second active ingredient selected from the group consisting of an antimicrobial agent, an anti-inflammatory agent, a biologic, a chemotherapy/anticancer agent, a cough and cold preparation, a dental hygiene product, a saliva stimulating agent, another anaesthetic agent, and an antiemetic.

22. The method of claim 21, wherein the second active ingredient is an antimicrobial agent selected from the group consisting of an antiviral agent, an antimycotic agent and an antibiotic; a cough and cold preparation selected from the group consisting of an antitussive, an expectorant, and a decongestant; or a dental hygiene product comprising a fluoride-releasing compound.

* * * * *